(12) United States Patent
Azimi

(10) Patent No.: US 10,030,058 B2
(45) Date of Patent: *Jul. 24, 2018

(54) MODULATING GAMMA-C-CYTOKINE ACTIVITY

(71) Applicant: Bioniz, LLC, Irvine, CA (US)

(72) Inventor: Nazli Azimi, San Juan Capistrano, CA (US)

(73) Assignee: BIONIZ, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/287,517

(22) Filed: Oct. 6, 2016

(65) Prior Publication Data

US 2017/0101452 A1  Apr. 13, 2017

Related U.S. Application Data

(60) Provisional application No. 62/239,761, filed on Oct. 9, 2015.

(51) Int. Cl.
| | | |
|---|---|---|
| A61K 8/64 | (2006.01) |
| A61K 38/00 | (2006.01) |
| C07K 14/54 | (2006.01) |
| C07K 14/55 | (2006.01) |
| A61Q 3/00 | (2006.01) |
| A61Q 19/00 | (2006.01) |
| A61Q 19/08 | (2006.01) |
| A61Q 7/00 | (2006.01) |

(52) U.S. Cl.
CPC ............... *C07K 14/54* (2013.01); *A61K 8/64* (2013.01); *A61Q 3/00* (2013.01); *A61Q 7/00* (2013.01); *A61Q 19/004* (2013.01); *A61Q 19/08* (2013.01); *C07K 14/5406* (2013.01); *C07K 14/5418* (2013.01); *C07K 14/5425* (2013.01); *C07K 14/5443* (2013.01); *A61K 38/00* (2013.01); *C07K 2319/02* (2013.01); *C07K 2319/30* (2013.01); *C07K 2319/31* (2013.01)

(58) Field of Classification Search
CPC ...... A61K 8/64; A61K 38/00; C07K 2319/02; C07K 2319/30; C07K 2319/31; C07K 14/55; C07K 14/5425; C07K 14/5418; C07K 14/5443

See application file for complete search history.

(56) References Cited

U.S. PATENT DOCUMENTS

| | | |
|---|---|---|
| 4,518,584 A | 5/1985 | Mark et al. |
| 5,700,913 A | 12/1997 | Taniguchi et al. |
| 5,795,966 A | 8/1998 | Grabstein et al. |
| 6,013,480 A | 1/2000 | Grabstein et al. |
| 6,028,186 A | 2/2000 | Tasset et al. |
| 6,127,387 A | 10/2000 | Huang et al. |
| 6,168,783 B1 | 1/2001 | Grabstein et al. |
| 6,261,559 B1 | 7/2001 | Levitt et al. |
| 6,307,024 B1 | 10/2001 | Novak et al. |
| 6,323,027 B1 | 11/2001 | Burkly et al. |
| 6,686,178 B2 | 2/2004 | Novak et al. |
| 6,770,745 B2 | 8/2004 | Burkly et al. |
| 6,793,919 B2 | 9/2004 | Mohler |
| 6,797,263 B2 | 9/2004 | Strom et al. |
| 6,811,780 B2 | 11/2004 | Furfine et al. |
| 6,838,433 B2 | 1/2005 | Serlupi-Crescenzi |
| 6,955,807 B1 | 10/2005 | Shanafelt et al. |
| 7,105,653 B2 | 9/2006 | Shanafelt et al. |
| 7,148,333 B2 | 12/2006 | Cox, III |
| 7,192,578 B2 | 3/2007 | Levitt et al. |
| 7,235,240 B2 | 6/2007 | Grabstein et al. |
| 7,314,623 B2 | 1/2008 | Grusby et al. |
| 7,347,995 B2 | 3/2008 | Strom et al. |

(Continued)

FOREIGN PATENT DOCUMENTS

| | | |
|---|---|---|
| CN | 1478098 A | 2/2004 |
| CN | 1703423 A | 11/2005 |

(Continued)

OTHER PUBLICATIONS

Antony, et al., "Interleukin-2-Dependent Mechanisms of Tolerance and Immunity In Vivo," J. Immunol. 176: 5255-5266, 2006.
Azimi, N., "Human T Cell Lymphotropic Virus Type I Tax Protein Trans-Activates Interleukin 15 Gene Transcription Through an NF-kappaB Site," Proc. Natl. Acad. Sci. USA 95:2452-2457, 1998.
Azimi, N., "Involvement of IL-15 in The Pathogenesis of Human T Lymphotropic Virus Type-I-Associated Myelopathy/Tropical Spastic Paraparesis: Implications for Therapy with a Monoclonal Antibody Directed to the IL-2/15Rbeta Receptor," J. Immunol. 163:4064-4072, 1999.

(Continued)

*Primary Examiner* — Robert S. Landsman
*Assistant Examiner* — Bruce D. Hissong
(74) *Attorney, Agent, or Firm* — Knobbe, Martens, Olson & Bear, LLP

(57) ABSTRACT

Embodiments relate to peptide antagonists of γc-family cytokines, which is associated with important human diseases, such as leukemia, autoimmune diseases, collagen diseases, diabetes mellitus, skin diseases, degenerative neuronal diseases and graft-versus-host disease (GvHD). Thus, inhibitors of γc-cytokine activity are valuable therapeutic and cosmetic agents as well as research tools. Traditional approaches to inhibiting γc-cytokine activity involve raising neutralizing antibodies against each individual γc-cytokine family member/receptor subunit. However, success has been limited and often multiple γc-cytokine family members co-operate to cause the disease state. Combinatorial use of neutralizing antibodies raised against each factor is impractical and poses an increased risk of adverse immune reactions. The present embodiments overcome these shortcomings by utilizing peptide antagonists based on the consensus γc-subunit binding site to inhibit γc-cytokine activity. Such approach allows for flexibility in antagonist design. In several embodiments, peptides exhibit Simul-Block activity, inhibiting the activity of multiple γc-cytokine family members.

8 Claims, 11 Drawing Sheets

(56) References Cited

U.S. PATENT DOCUMENTS

| | | |
|---|---|---|
| 7,423,123 B2 | 9/2008 | Boisvert et al. |
| 7,473,765 B2 | 1/2009 | Novak et al. |
| 7,645,449 B2 | 1/2010 | Stassi et al. |
| 7,700,088 B2 | 4/2010 | Levitt et al. |
| 7,731,946 B2 | 6/2010 | Grusby et al. |
| 7,785,580 B2 | 8/2010 | Pan et al. |
| 7,910,123 B2 | 3/2011 | McKay |
| 7,959,908 B2 | 6/2011 | Nelson et al. |
| 8,110,180 B2 | 2/2012 | Novak et al. |
| 8,211,420 B2 | 7/2012 | Bondensgaard |
| 8,455,449 B2 | 6/2013 | Tagaya |
| 9,133,243 B2 | 9/2015 | Tagaya |
| 9,133,244 B2 | 9/2015 | Tagaya |
| 9,670,672 B2 | 1/2017 | Tagaya |
| 9,675,672 B2 | 6/2017 | Tagaya |
| 2002/0114781 A1 | 8/2002 | Strom et al. |
| 2003/0049798 A1 | 3/2003 | Carter et al. |
| 2003/0108549 A1 | 6/2003 | Carter et al. |
| 2004/0009150 A1 | 1/2004 | Nelson et al. |
| 2004/0136954 A1 | 7/2004 | Grusby et al. |
| 2005/0124044 A1 | 6/2005 | Cunningham et al. |
| 2006/0034892 A1 | 2/2006 | Ueno |
| 2006/0039902 A1 | 2/2006 | Young et al. |
| 2006/0236411 A1 | 10/2006 | Dreher et al. |
| 2006/0263857 A1 | 11/2006 | Lefrancois et al. |
| 2007/0048266 A1 | 3/2007 | Nelson |
| 2008/0038275 A1 | 2/2008 | Martin |
| 2008/0166338 A1 | 7/2008 | Leonard |
| 2009/0136511 A1 | 5/2009 | Santos Savio et al. |
| 2009/0148403 A1 | 6/2009 | Bosivert et al. |
| 2009/0253864 A1 | 10/2009 | Peschke et al. |
| 2009/0258357 A1 | 10/2009 | Ruben |
| 2010/0099742 A1 | 4/2010 | Stassi |
| 2010/0135958 A1 | 6/2010 | Hwu |
| 2010/0196309 A1 | 8/2010 | Bondensgaard et al. |
| 2010/0266531 A1 | 10/2010 | Hsieh |
| 2011/0081327 A1 | 4/2011 | Nicolette |
| 2011/0142833 A1 | 6/2011 | Young |
| 2011/0245090 A1 | 10/2011 | Abbas |
| 2011/0311475 A1 | 12/2011 | Borte |
| 2012/0329728 A1 | 12/2012 | Tagaya |
| 2013/0095102 A1 | 4/2013 | Levin |
| 2013/0217858 A1 | 8/2013 | Bioniz |
| 2016/0000877 A1 | 1/2016 | Bionz |
| 2016/0306918 A1 | 10/2016 | Azimi |
| 2017/0051015 A1 | 2/2017 | Bionz |
| 2017/0101452 A1 | 4/2017 | Tagaya |
| 2017/0204153 A1 | 7/2017 | Tagaya |
| 2017/0240607 A1 | 8/2017 | Bioniz |

FOREIGN PATENT DOCUMENTS

| | | |
|---|---|---|
| CN | 103501805 A | 1/2014 |
| EP | 1525213 B1 | 4/2005 |
| EP | 2665486 A1 | 11/2013 |
| JP | 2004-525076 | 8/2004 |
| JP | 2005-508179 | 3/2005 |
| WO | WO 8702990 A1 | 5/1987 |
| WO | WO 2003040313 A1 | 9/2003 |
| WO | WO 03/087320 A2 | 10/2003 |
| WO | WO 2004084835 A2 | 10/2004 |
| WO | WO 2005014642 A2 | 2/2005 |
| WO | WO 2005030196 A2 | 4/2005 |
| WO | WO 2005067956 A2 | 7/2005 |
| WO | WO 2005112983 A2 | 12/2005 |
| WO | WO 2006105538 A2 | 5/2006 |
| WO | WO 2006111524 A2 | 10/2006 |
| WO | WO 2006113331 A1 | 10/2006 |
| WO | WO 2008049920 A2 | 2/2008 |
| WO | WO 2009108341 A1 | 3/2009 |
| WO | WO 2009100035 A2 | 8/2009 |
| WO | WO 2009132821 A1 | 11/2009 |
| WO | WO 2010039533 A2 | 4/2010 |
| WO | WO 2010076339 A1 | 7/2010 |
| WO | WO 2010103038 A1 | 9/2010 |
| WO | WO 2010133828 A1 | 11/2010 |
| WO | WO 2011070214 A2 | 6/2011 |
| WO | WO 2011133948 A2 | 10/2011 |
| WO | WO 2012006585 A2 | 1/2012 |
| WO | WO 2012012531 A2 | 1/2012 |
| WO | WO 2012/099886 | 7/2012 |
| WO | WO 2012/175222 A1 | 12/2012 |
| WO | WO 2015/089217 | 6/2015 |
| WO | WO 2015/089217 A2 | 6/2015 |
| WO | WO 2015/089217 A3 | 6/2015 |
| WO | WO 2017/062685 A1 | 4/2017 |

OTHER PUBLICATIONS

Azimi, N., et al., "How Does Interleukin 15 Contribute to the Pathogenesis of HTLV Type-1 Associated Myelopathy/Tropical Spastic Paraparesis?" AIDS Res. Hum. Retroviruses 16:1717-1722, 2000.

Azimi, N., et al., "IL-15 Plays a Major Role in the Persistence of Tax-specific CD8 Cells in HAM/TSP patients," Proc. Natl. Acad. Sci. 98:14559-14564, 2001.

Bazan, J.F., "Hematopoietic Receptors and Helical cytokines," Immunol. Today 11:350-354, 1990.

Bernand, et al Identification of an Interleukin-15α Receptor-binding Site on Human Interleukin-15*, The Journal of Biological Chemistry (2004)279:24313-24322.

Bettini, M. and D.A. Vignali, "Regulatory T Cells and Inhibitory Cytokines in Autoimmunity," Curr. Opin. Immunol. 21:612-618, 2009.

Bodd, M., et al., "HLA-DQ2-Restricted Gluten-Reactive T cells Produce IL-21 but not IL-17 or IL-22," Mucosal Immunol. 3:594-601, 2010.

Bonsch, et al, Species-specific Agonist/Antagonist Activities of Human Interleukin-4 Variants Suggest Distinct Ligand Binding Properties of Human and Murine Common Receptor γ Chain*, The Journal of Biological Chemistry (1995) 270:8452-8457.

De Rezende, L.C., et al., "Regulatory T Cells as a Target for Cancer Therapy," Arch. Immunol. Ther. Exp. 58:179-190, 2010.

Decision of Rexamination Received Jun. 27, 2017 in Chinese Application 201280010348.8.

Definition of composite from www.merriam-sebster.com/dictionary/composite, pp. 1-5. Accessed Feb. 17, 2015.

Definition of derivative from http://cancerweb.ncl.ac.uk/omd/about.html, pp. 1-5. Accessed Jul. 7, 2005.

Dubois, S., et al., "IL-15R alpha Recycles and Presents IL-15 in Trans to Neighboring Cells," Immunity 17:537-547, 2002.

Extended EP Search report dated May 22, 2014 for PCT/US2012/021566.

Fehniger, T.A., "Fatal Leukemia in Interleukin 15 Transgenic Mice Follows Early Expansions in Natural Killer and Memory Phenotype CD8+ T Cells," J. Exp. Med. 193:219-231, 2001.

Final Office Action dated Feb. 24, 2015 for U.S. Appl. No. 13/868,725.

Final Office Action dispatched Nov. 29, 2016 for JP Patent Application 2013-550541.

Fisher, A.G. et al., "Lymphoproliferative disorders in an IL-7 transgenic mouse line," Leukemia 2, 1993, pp. 66-68.

Gong, J.H. et al., Characterization of a human cell line (NK-92) with phenotypical and functional characteristics of activated natural killer cells. Leukemia 8, 1994, pp. 652-658.

Hennighausen, L., and G.W. Robinson, "Interpretation of Cytokine Signaling Through the Transcription Factors STAT5A and STAT5B," Genes Dev. 22:711-721, 2008.

Hodge, D.L., et al., IL-2 and IL-12 Alter NK Cell Responsiveness to IFN-Gamma-Inducible Protein 10 by Down-Regulating CXCR3 Expression, J. Immun. 168:6090-6098, 2002.

International Preliminary Report on Patentability dated Jul. 23, 2013 for PCT/US2012/021566.

International Preliminary Report on Patentability dated Jun. 23, 2016 for PCT/US2012/062870.

International Search Report and Written Opinion dated Apr. 7, 2012 for PCT/US2012/021566.

(56) References Cited

OTHER PUBLICATIONS

International Search Report and Written Opinion dated Jan. 17, 2017 for PCT/US2016/055845.
International Search Report dated Jun. 26, 2015 for PCT/US14/69597.
Klingemann, H.G. et al., "A cytotoxic NK-cell line (NK-92) for ex vivo purging of leukemia from blood," Blood Marrow Transplant 2, 1996, pp. 68-75.
Krause, C.D. And S. Pestka, "Evolution of the Class 2 Cytokines and Receptors, and Discovery of New Friends and Relatives," Pharmacol. and Therapeutics 106:299-346, 2005.
Kundig, T.M. et al. "Immune Responses of the interleukin-2-deficient mice," Science 262, 1993, pp. 1059-1061.
Le Buanec, H., et al., "Control of Allergic Reactions in Mice by an Active Anti-Murine IL-4 Immunization," Vaccine 25:7206-7216, 2007.
Littman, D.R., and A.Y. Rudensky, "Th17 and Regulatory T Cells in Mediating and Restraining Inflammation," Cell 140(6):845-858, 2010.
Miyagawa, F., et al., "IL-15 Serves as a Costimulator in Determining the Activity of Autoreactive CD8 T Cells in an Experimental Mouse Model of Graft-Versus-Host-Like Disease," J. Immunol. 181:1109- 1119, 2008.
NCBI Accession No. ABF82250, Accessed Aug. 11, 2014.
NCBI Accession No. BAA96385, Accessed Aug. 11, 2014.
NCBI Accession No. NP_999580, Accessed Aug. 11, 2014.
NCBI Accession No.ACT78884, Accessed Aug. 11, 2014.
NCBI Accession No. NP_999288, Accessed Aug. 11, 2014.
Noguchi, M., et al., "Interleukin 2 Receptor Gamma Chain Mutation Results in X-linked Severe Combined Immunodeficiency in Humans," Cell 73:147-157, 1993.
Notice of Acceptance dated Oct. 19, 2016 for AU Application 2012207456.
Notice of Allowance dated Feb. 19, 2013 for U.S. Appl. No. 13/589,017.
Notice of Allowance dated Feb. 6, 2017 for U.S. Appl. No. 14/852,240.
Notice of Allowance dated May 11, 2015 for U.S. Appl. No. 13/868,725.
Notice of Allowance dated May 4, 2015 for U.S. Appl. No. 13/980,305.
Notification of Re-examination dated Mar. 24, 2017 for CN Patent Application 201280010348.8.
O'Shea, J.J., "Targeting the Jak/STAT Pathway for Immunosuppression," Ann. Rheum. Dis. 63:(Suppl. II):ii67-71, 2004.
Office Action dated Aug. 18, 2014 for U.S. Appl. No. 13/868,725.
Office Action dated Aug. 3, 2017for U.S. Appl. No. 15/103,804.
Office Action dated Aug. 8, 2017for U.S. Appl. No. 15/585,666.
Office Action dated Jan. 26, 2016 for JP Patent Application 2013-550541.
Office Action dated Jul. 2, 2014 for corresponding CN Application 201280010348.8.
Office Action dated Jul. 24, 2017 in U.S. Appl. No. 15/179,900.
Office Action dated Jul. 4, 2016 for Chinese Patent Application No. 201280010348.8.
Office Action dated Nov. 12, 2014 for U.S. Appl. No. 13/980,305.
Office Action dated Oct. 26, 2016 in EP Patent Application No. 12736203.6.
Office Action dated Oct. 18, 2014 for U.S. Appl. No. 13/868,725.
Office Action dated Oct. 22, 2015 for AU Application 2012207456.
Office Action dated Oct. 27, 2015 for Chinese Patent Application No. 201280010348.8.
Office Action dated Sep. 6, 2016 for U.S. Appl. No. 14/852,240.
Office Action dated Apr. 28, 2015 for Chinese Patent Application No. 201280010348.8.
Oh, U., and S. Jacobson, "Treatment of HTLV-I-Associated Myelopathy / Tropical Spastic Paraparesis: Towards Rational Targeted Therapy," Neurol. Clin. 26:781-785, 2008.
Orzaez, M., et al., "Peptides and Peptide Mimics as Modulators of Apoptotic Pathways," Chem. Med. Chem. 4:146-160, 2009.
Paul, W.E., "Pleiotropy and Redundancy: T Cell-Derived Lymphokines in the Immune Response," Cell 57:521-524, 1989.
Pesu, M., "Jak3, Severe Combined Immunodeficiency, and a New Class of Immunosuppressive Drugs," Immunol. Rev. 203:127-142, 2005.
Pesu, M., Laurence, et al., "Therapeutic Targeting of Janus Kinases," Immunol. Rev. 223:132-142, 2008.
Restriction Requirement dated Feb. 28, 2017 for U.S. Appl. No. 15/179,900.
Restriction Requirement dated Jun. 24, 2014 for U.S. Appl. No. 13/980,305.
Restriction Requirement dated Mar. 24, 2017 for U.S. Appl. No. 15/103,804.
Restriction Requirement dated May 9, 2014 for U.S. Appl. No. 13/868,725.
Rochman, Y., et al., "New Insights into the Regulation of T Cells by Gamma C Family Cytokines," Nat. Rev. Immunol. 9:480-490, 2009.
Sakaguchi, S., et al., "Regulatory T Cells and Immune Tolerance," Cell 133:775-787, 2008.
Sato, N., et al., "Development of an IL-15-Autocrine CD8 T-cell Leukemia in IL-15 Transgenic mice requires the cis-expression of IL-15R apha," Blood 2011.
Sugamura, K., et al., "The Common Gamma-Chain for Multiple Cytokine Receptors," Adv. Immunol. 59:225-277, 1995.
Sugamura, K., et al., "The Interleukin-2 Receptor Gamma Chain: Its Role in the Multiple Cytokine Receptor Complexes and T Cell Development in XSCID," Annu. Rev. Immunol. 14:179-205, 1996.
Supplementary European Search Report dated May 22, 2014 for European Application No. 12784848.9.
Tagaya, Y., "Memory CD8 T Cells Now Join 'Club 21," J. Leuk. Biol. 87:13-15, 2010.
Tagaya, Y., et al., "Identification of a Novel Receptor/Signal Transduction Pathway for IL-15/T in Mast Cells," Embo J. 15:4928-4939, 1996.
Takai, K. et al., The Wheat-Germ Cell-Free Expression System, Curr. Pharm. Biotechnol. 11, 2010, pp. 272-278.
Takeshita, T., et al., "Cloning of the Gamma Chain of the Human IL-2 Receptor," Science 257:379-382, 1992.
Tanaka, T., et al., "A Novel Monoclonal Antibody Against Murine IL-2 Receptor Beta-Chain. Characterization of Receptor Expression in Normal Lymphoid Cells and EL-4 Cells," J. Immunol. 147:2222-2228, 1991.
Waldmann, T.A., Anti-Tac (daclizumab, Zenapax) in the Treatment of Leukemia, Autoimmune Diseases, and in the Prevention of Allograft Rejection: A 25-Year Personal Odyssey, J. Clin. Immunol. 27:1-18, 2007.
Water is naturally occurring from www.biology-online.org/dictionary/Water, pp. 1-3, Accesssed Apr. 24, 2014.
Hines, L et at. Interleukin 15, partial [synthetic construct]. NCBI PDS Accession No. AAX36174, interleukin 15, partial [synthetic construct]. Submitted Jan. 5, 2005; downloaded from the internet <https://www.ncbi.nlm.nih.gov/protein/60811495/> on Dec. 14, 2016, p. 1.
Bernard, J., et al., Identification of an Interleukin-15α Receptor-binding Site on Human Interleukin-15*, The Journal of Biological Chemistry, vol. 279, No. 23, pp. 24313-24322, 2004.
International Preliminary Report on Patentability dated Jun. 14, 2016 for PCT/US2012/062870.
International Search Report and Written Opinion of the International Searching Authority in International Application No. PCT/US2012/021566 dated May 10, 2012.
Notice of Allowance dated Dec. 15, 2017 in U.S. Appl. No. 15/179,900.
Notice of Allowance dated Dec. 19, 2017 for U.S. Appl. No. 15/103,804.
Office Action Dated Nov. 22, 2017 in Canadian Application No. 2,824,51.
Final Office Action dated Dec. 13, 2017 for U.S. Appl. No. 15/585,666.
Restriction Requirement dated Jan. 26, 2018 for U.S. Appl. No. 15/474,312.

Alignment of the D-helix region sequence of human γc-family cytokines

| | | | | | | | | | | | | | | | | | SEQ ID NO: |
|---|---|---|---|---|---|---|---|---|---|---|---|---|---|---|---|---|---|
| IL-15 | I | K | E | F | L | Q | S | F | V | H | I | V | Q | M | F | I | N | T | S | stop | | | 4 |
| IL-2 | I | V | E | F | L | N | R | W | I | T | F | C | Q | S | I | I | S | T | L | T | stop | | 5 |
| IL-21 | P | K | E | F | L | E | R | F | K | S | L | L | Q | K | M | I | H | Q | H | L | S | | 6 |
| IL-4 | E | N | F | L | E | R | L | K | T | I | M | R | E | K | Y | S | K | C | S | S | | 7 |
| IL-9 | A | L | T | F | L | E | S | L | L | E | L | F | Q | K | E | K | M | R | G | M | R | | 8 |
| IL-7 | D | L | C | F | L | K | R | L | - | L | - | Q | E | I | K | T | C | W | N | K The consensus sequence for the γc- and the IL-2/IL-15-box.

| | 1 | 2 | 3 | 4 | 5 | 6 | 7 | 8 | 9 | 10 | 11 | 12 | 13 | 14 | 15 | 16 | 17 | 18 | 19 | SEQ ID NO: |
|---|---|---|---|---|---|---|---|---|---|---|---|---|---|---|---|---|---|---|---|---|
| γc-Box | | | D/E | F | L | Polar E QN | Polar S/R | Non-polar | Non-polar I,K | | Aliphatic L/I | Non-polar | Q | Charged | | I/K | | | | 10 |
| IL-2/IL-15 box | | | | | | | | | | | | | Q | | | I | | T | S | 11 |

| SEQ ID NO | Peptide | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|
| 3 | SEQ ID NO: 3 | Pro | Lys | Glu | Phe | Leu | Glu | Arg | Phe | Val | His | Leu | Val | Gln | Met | Phe | Ile | His | Gln | Ser | Leu | Ser |
| 4 | IL-15 | Ile | Lys | Glu | Phe | Leu | Gln | Ser | Phe | Val | His | Ile | Val | Gln | Met | Phe | Ile | Asn | Thr | Ser | | |
| 5 | IL-2 | Ile | Val | Glu | Phe | Leu | Asn | Arg | Trp | Ile | Thr | Phe | Cys | Gln | Ser | Ile | Ile | Ser | Thr | Leu | Thr | |
| 6 | IL-21 | Pro | Lys | Glu | Phe | Leu | Glu | Arg | Phe | Lys | Ser | Leu | Leu | Gln | Lys | Met | Ile | His | Gln | His | Leu | Ser |
| 7 | IL-4 | Leu | Glu | Asn | Phe | Leu | Glu | Arg | Leu | Lys | Thr | Ile | Met | Arg | Glu | Lys | Tyr | Ser | Lys | Cys | Ser | Ser |
| 8 | IL-9 | Ala | Leu | Thr | Phe | Leu | Glu | Ser | Leu | Leu | Glu | Leu | Phe | Gln | Lys | Glu | Lys | Met | Arg | Gly | Met | Arg |
| 9 | IL-7 | Asp | Leu | Cys | Phe | Leu | Lys | Arg | Leu | Leu | Gln | Glu | Ile | Lys | Thr | Cys | Trp | Asn | Lys | Ile | Leu | |

MODULATING GAMMA-C-CYTOKINE ACTIVITY

PRIORITY AND CROSS REFERENCE TO RELATED APPLICATIONS

This application claims the benefit of U.S. Provisional Application No. 62/239,761, filed Oct. 9, 2015, which is hereby incorporated by reference in its entirety.

SEQUENCE LISTING IN ELECTRONIC FORMAT

The present application is being filed along with a Sequence Listing as an ASCII text file via EFS-Web. The Sequence Listing is provided as a file entitled BION006ASEQLIST.txt, created and last saved on Oct. 6, 2016, which is 5,980 bytes in size. The information in the electronic format of the Sequence Listing is incorporated herein by reference in its entirety in accordance with 35 U.S.C. § 1.52(e).

FIELD

Some embodiments relate to peptide antagonists of γc-family cytokines, a group of mammalian cytokines that are mainly produced by epithelial, stromal and immune cells and control the normal and pathological activation of a diverse array of lymphocytes. Some embodiments also relate to the therapeutic uses of such peptides for the treatment of certain human diseases. The present embodiments also relate to the cosmeceutical applications of such peptides. Description of target diseases, cosmeceutical applications, as well as methods of administration, production, and commercialization of the peptides are disclosed.

BACKGROUND

Cytokines are a diverse group of soluble factors that mediate various cell functions, such as, growth, functional differentiation, and promotion or prevention of programmed cell death (apoptotic cell death). Cytokines, unlike hormones, are not produced by specialized glandular tissues, but can be produced by a wide variety of cell types, such as epithelial, stromal or immune cells.

The γc-family cytokines are a group of mammalian cytokines that are mainly produced by epithelial, stromal and immune cells and control the normal and pathological activation of a diverse array of lymphocytes. These cytokines are critically required for the early development of T cells in the thymus as well as their homeostasis in the periphery.

SUMMARY

In some embodiments, a composite peptide that comprises amino acid sequences of at least two interleukin (IL) protein gamma-c-box D-helix regions, wherein the composite peptide comprises the amino acid sequence P-K-E-F-L-E-R-F-V-H-L-V-Q-M-F-I-H-Q-S-L-S (SEQ ID NO: 3). In some embodiments, the composite peptide inhibits the activity of two or more γc-cytokines selected from the group consisting of IL 2, IL 4, IL 7, IL 9, IL 15, and IL 21. In some embodiments, the composite peptide inhibits the activity of at least IL-15 and IL-21.

In some embodiments, the composite peptide comprises a signal peptide. In some embodiments, the composite peptide is further conjugated to one or more additional moieties at the N terminus, C terminus or a side residue of the composite peptide. In some embodiments of the composite peptide, the one or more additional moieties are selected from the group consisting of bovine serum albumin (BSA), albumin, Keyhold Limpet Hemocyanin (KLH), Fc region of IgG, a biological protein that functions as scaffold, an antibody against a cell-specific antigen, a receptor, a ligand, a metal ion, and Poly Ethylene Glycol (PEG).

In some embodiments, a pharmaceutical composition is provided. In some embodiments, the pharmaceutical composition comprises a therapeutically effective amount of a peptide conjugate or a derivative thereof, and a pharmaceutically acceptable carrier, diluent, excipient or combination thereof, wherein the peptide conjugate or the derivative thereof modulates the activity of two or more γc-cytokines selected from the group consisting of IL 2, IL 4, IL 7, IL 9, IL 15, and IL 21, wherein the peptide conjugate comprises the amino acid sequence P-K-E-F-L-E-R-F-V-H-L-V-Q-M-F-I-H-Q-S-L-S (SEQ ID NO: 3), and wherein the derivative thereof comprises a peptide sequence sharing at least 90% identity with the amino acid sequence of SEQ ID NO: 3.

In some embodiments of the pharmaceutical composition, the peptide conjugate or the derivative thereof inhibits the activity of two or more γc-cytokines selected from the group consisting of IL 2, IL 4, IL 7, IL 9, IL 15, and IL 21. In some embodiments of the pharmaceutical composition, the peptide conjugate or the derivative thereof further comprises an additional conjugate at the N termini, C termini or a side residues thereof.

In some embodiments of the pharmaceutical composition, the peptide conjugate or the derivative thereof further comprises a signal peptide. In some embodiments, the pharmaceutical composition further comprises a protein that stabilizes the structure of the peptide conjugate or the derivative thereof and improves its biological activity, wherein the protein is selected from the group consisting of bovine serum albumin (BSA), albumin, Fc region of immunoglobulin G (IgG), biological proteins that function as scaffold, Poly Ethylene Glycol (PEG), and derivatives thereof. In some embodiments of the pharmaceutical composition, the derivative thereof comprises a peptide sequence sharing at least 95% identity with the amino acid sequence of SEQ ID NO: 3.

In some embodiments, a method for blocking signaling by two or more γc cytokine family members is provided. In some embodiments, the method comprises contacting a cell with a pharmaceutical composition provided herein.

In some embodiments, a method inhibiting γc cytokine binding to a γc subunit is provided. In some embodiments, the method comprises contacting a γc subunit of a cell with a pharmaceutical composition provided herein.

In some embodiments, a method of treating a γc cytokine-mediated disease is provided. In some embodiments, the method comprises administering a pharmaceutical composition of provided to a subject in need thereof, wherein the γc cytokine-mediated disease is selected from the group consisting of CD4 leukemia, CD8 leukemia, LGL leukemia, systemic lupus erythematosis, Sjögren's syndrome, Wegener's granulomatosis, Celiac disease, Hashimoto's thyroiditis, rheumatoid arthritis, diabetes mellitus, psoriasis, multiple sclerosis, uvietis, inflammation of the eye, and graft-versus-host disease (GvHD).

In some embodiments, a method of treating an HTLV-1-associated myelopathy (HAM)/tropical spastic paraparesis (TSP) associated disease is provided. In some embodiments, the method comprises administering a pharmaceutical composition provided herein to a subject in need thereof, wherein the HAM/TSP associated disease is selected from the group consisting of Adult T-cell Leukemia (ATL), HTLV-associated Myelopathy/Tropical Spastic Paraparesis (HAM/TSP), and other non-neeoplastic inflammatory diseases associated with HTLV such as uveitis (HU), arthropathy, pneumopathy, dermatitis, exocrinopathy, and myositis.

In some embodiments, a method of treating an inflammatory respiratory disease is provided. In some embodiments, the method comprises administering a pharmaceutical composition provided herein to a subject in need thereof, wherein the inflammatory respiratory disease is selected from the group consisting of asthma, sinusitis, hay fever, bronchitis, chronic obstructive pulmonary disease (COPD), allergic rhinitis, acute and chronic otitis, and lung fibrosis.

In some embodiments, a method of treating a cosmetic condition is provided. In some embodiments, the method comprises administering a pharmaceutical composition provided herein to a subject in need thereof, wherein the cosmetic disease is selected from the group consisting of acne, hair loss, sunburn, nail maintenance, and appearance of aging.

In some embodiments, a kit for treating a condition in a patient is provided. In some embodiments, the condition is a γc cytokine-mediated disease, an HTLV-1-associated myelopathy (HAM)/tropical spastic paraparesis (TSP) associated disease, an inflammatory respiratory disease, a cosmetic condition, or a combination thereof.

In some embodiments, the kit comprises a pharmaceutical composition, wherein the pharmaceutical composition comprises a therapeutically effective amount of a peptide conjugate, or a derivative thereof, and a pharmaceutically acceptable carrier, diluent, excipient or combination thereof, wherein the peptide conjugate or the derivative thereof modulates the activity of two or more γc-cytokines selected from the group consisting of IL 2, IL 4, IL 7, IL 9, IL 15, and IL 21, wherein the peptide conjugate comprises the amino acid sequence P-K-E-F-L-E-R-F-V-H-L-V-Q-M-F-I-H-Q-S-L-S (SEQ ID NO: 3), and wherein the derivative thereof comprises a peptide sequence sharing at least 90% identity with the amino acid sequence of SEQ ID NO: 3.

In some embodiments of the kit, the condition is one or more of CD4 leukemia, CD8 leukemia, LGL leukemia, systemic lupus erythematosis, Sjögren's syndrome, Wegener's granulomatosis, Celiac disease, Hashimoto's thyroiditis, rheumatoid arthritis, diabetes mellitus, psoriasis, multiple sclerosis, uvietis, inflammation of the eye, graft-versus-host disease (GvHD), Adult T-cell Leukemia (ATL), HTLV-associated Myelopathy/Tropical Spastic Paraparesis (HAM/TSP), and other non-neeoplastic inflammatory diseases associated with HTLV such as uveitis (HU), arthropathy, pneumopathy, dermatitis, exocrinopathy, myositis, asthma, sinusitis, hay fever, bronchitis, chronic obstructive pulmonary disease (COPD), allergic rhinitis, acute and chronic otitis, and lung fibrosis, acne, hair loss, sunburn, nail maintenance, or appearance of aging.

BRIEF DESCRIPTION OF THE DRAWINGS

FIG. 1A shows an alignment of the D-helix region of human γc-cytokine family members.

FIG. 1B depicts the γc-box (SEQ ID NO: 10) and IL-2/IL-15 box (SEQ ID NO: 11) motifs which give rise to the consensus sequence around the D-helix region of the γc-cytokines.

FIG. 5 shows the alignment of the sequence of SEQ ID NO: 3 to the D-helix regions of different human γc-cytokine family members. The shaded areas represent amino acid sequences of the human γc-cytokine family members that are identical to their corresponding amino acids in the sequence of SEQ ID NO: 3.

DETAILED DESCRIPTION

Overview

Figure 2:
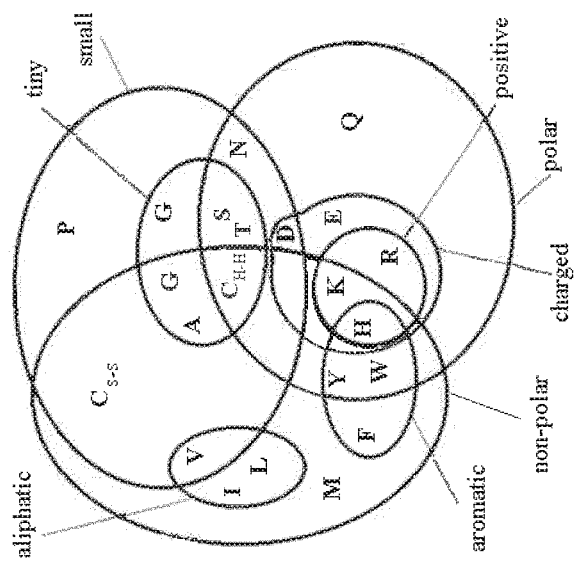
FIG. 2 depicts a diagramed representation of the biochemical properties of amino acids.

More than 100 cytokines have been identified so far and are considered to have developed by means of gene duplications from a pool of primordial genes (See Bazan, J. F. 1990, Immunol. Today 11:350-354). In support of this view, it is common for a group of cytokines to share a component in their multi-subunit receptor system. The most well-documented shared cytokine subunit in T cells is the common γ subunit (γc-subunit).

The γc-subunit is shared by 6 known cytokines (Interleukin-2 (IL-2), Interleukin-4 (IL-4), Interleukin-7 (IL-7), Interleukin-9 (IL-9), Interleukin-15 (IL-15), and Interleukin-21 (IL-21), collectively called the "γc-cytokines" or "γc-family cytokines") and plays an indispensable role in transducing cell activation signals for all these cytokines. Additionally, for each of the γc-cytokines, there are one or two private cytokine-specific receptor subunits that when complexed with the γc-subunit, give rise to a fully functional receptor. (See Rochman et al., 2009, Nat Rev Immunol. 9: 480-90.)

The γc-family cytokines are a group of mammalian cytokines that are mainly produced by epithelial, stromal and immune cells and control the normal and pathological activation of a diverse array of lymphocytes. These cytokines are critically required for the early development of T cells in the thymus as well as their homeostasis in the periphery. For example, in the absence of the γc-subunit, T, B and NK cells do not develop in mice. (See Sugamura et al., 1996, Annu. Rev. Immunol. 14:179-205).

The γc-cytokines are important players in the development of the lymphoid cells that constitute the immune system, particularly T, B, and NK cells. Further, γc-cytokines have been implicated in various human diseases. Thus, factors that inhibit γc-cytokine activity would provide useful tools to elucidate the developmental mechanism of subsets of lymphocytes and to treat immune disorders and γc-cytokine-mediated diseases.

Germ line depletion of the genes encoding the γc-subunit in mice or mutations of γc-subunit in humans are known to cause severe combined immunodeficiency (SCID) by disrupting the normal appearance or function of NK, T, and B cells. The importance of the γc-subunit in the signal transduction of the γc-cytokines, IL-2, -4, -7, -9, 15, -21, is indicated in studies demonstrating the a of response of lymphocytes from these mice and human patients to the γc-cytokines (reviewed in Sugamura et al., 1995 Adv. Immunol. 59:225-277). This indicates that disruption of the interaction between the γc-subunit and a γc-cytokine would efficiently block the intracellular signaling events by the γc-cytokine family members. Therefore antagonist peptides according to the present embodiments are expected to effectively block the pathogenic changes in humans suffering from the diseases mediated by misregulation of the γc-cytokine family members.

As an alternative to antibody-mediated approaches for modulating the activity of individual γc-cytokines, Applicants have devised novel, low molecular weight compounds herein referred to as "Simul-Block", which suppress the activity of multiple γc-cytokines. These low molecular weight compounds, which include both chemicals and peptides, are less immunogenic than antibodies. These properties distinguish Simul-Block as a more efficient strategy for mediating γc-cytokine activity in clinical interventions.

Pathologies Associated with the γc-Cytokines

Recent studies have indicated that dysregulation of expression and dysfunction of the γc-cytokines could lead to a wide variety of human immunologic and hematopoietic diseases.

IL-2

While IL-2 was historically considered a prototype T cell growth factor, the generation of a knockout mouse lacking IL-2 expression revealed that IL-2 is not critical for the growth or developmental of conventional T cells in vivo. Over-expression of IL-2, however, leads to a preferential expansion of a subset of T-cells; the regulatory T cells (T-regs). (See Antony et al., 2006, J. Immunol. 176:5255-66.) T-regs suppress the immune responses of other cells and thus act to maintain peripheral tolerance (reviewed in Sakaguchi et al., 2008, Cell 133:775-87). Breakdown of peripheral tolerance is thought to cause autoimmune diseases in humans.

Thus, the immunosuppressive function of T-regs is thought to prevent the development of autoimmune diseases (See Sakaguchi et al., 2008, Cell 133:775-87). T-regs have also been implicated in cancer, where solid tumors and hematologic malignancies have been associated with elevated numbers of T-regs (See De Rezende et al., 2010, Arch. Immunol. Ther. Exp. 58:179-190).

IL-4

IL-4 is a non-redundant cytokine involved in the differentiation of T helper cells into the Th2 (T-helper type 2) subset, which promotes the differentiation of premature B cells into IgE producing plasma cells. IgE levels are elevated in allergic asthma. Thus, IL-4 is implicated in the development of allergic Asthma. Antibodies targeting IL-4 can be used to treat or even prevent the onset of allergic asthma. (See Le Buanec et al., 2007, Vaccine 25:7206-16.)

IL-7

IL-7 is essential for B cell development and the early development of T cells in the thymus. In mice, the abnormal expression of IL-7 causes T-cell-associated leukemia. (See Fisher et al., 1993, Leukemia 2:S66-68.) However, in humans, misregulation of IL-7 does not appear to cause T-cell-associated leukemia. In humans, up-regulation of IL-7 either alone or in combination with another γc-cytokine family member, IL-15, has been implicated in Large Granular Lymphocyte (LGL) leukemia.

IL-9

The role of IL-9 is still rather uncharacterized compared to other γc-cytokine family members. Mice depleted of the IL-9 gene appear normal and do not lack any subsets of cells in the lymphoid and hematopoietic compartments. Recent studies, however, reveal an in vivo role for IL-9 in the generation of Th17 (T-helper induced by interleukin-17) cells (See Littman et al., 2010, Cell 140(6):845-58; and Nowak et al., 2009, J. Exp. Med. 206: 1653-60).

IL-15

IL-15 is critically involved in the development of NK cells, NK-T cells, some subsets of intraepithelial lymphocytes (IELs), γδ-T cells, and memory-phenotype CD8 T-cells (See Waldmann, 2007, J. Clin. Immunol. 27:1-18; and Tagaya et al., 1996, EMBO J. 15:4928-39.) Over-expression of IL-15 in mice leads to the development of NK-T cell and CD8 cell type T cell leukemia (See Fehniger et al., 2001, J. Exp. Med. 193:219-31; Sato et al. 2011 Blood in press). These experimentally induced leukemias appear similar to LGL (large-granular lymphocyte) leukemia in humans, since in both instances the leukemic cells express CD8 antigen.

It is also suspected that IL-15-mediated autocrine mechanisms may be involved in the leukemic transformation of CD4 T lymphocytes. (See Azimi et al., 1998, Proc. Natl. Acad. Sci. 95:2452-7; Azimi et al., 1999, J. Immunol. 163:4064-72; Azimi et al., 2000, AIDS Res. Hum. Retroviruses 16:1717-22; and Azimi et al., 2001, Proc. Natl. Acad. Sci. 98:14559-64). For example, CD4-tropic HTLV-I, which causes Adult T cell leukemia in humans, induces autocrine growth of virus-transformed T cells through the production of IL-15 and IL-15Rα (Azimi et al., 1998, Proc. Natl. Acad. Sci. 95:2452-7).

In addition to leukemic transformation, recent studies implicate IL-15 in the pathological development of Celiac disease (CD), an autoimmune disease. IL-15 is known to stimulate the differentiation of NK, CD8 and intestinal intraepithelial lymphocyte (IEL) cells into lymphokine-activated killer (LAK) cells by inducing the expression of cytolytic enzymes (i.e., Granzyme and Perforin) as well as interferon-γ. Celiac Disease (denoted CD from herein) is an immune-mediated enteropathy that is triggered by the consumption of gluten-containing food in individuals that express specific HLA-DQ alleles.

The prevalence of this disease is 1% in the western population. The only current treatment for CD is the complete elimination of gluten from the patient's diet. The pathology of CD is mainly caused by extensive damage to the intestinal mucosa, which is caused by activated CD8 T cells that have infiltrated to the intestinal lamina propria. These CD8 T cells appear to be activated through mechanisms involving IL-15. One recent publication demonstrated in mice that ectopic over-expression of IL-15 by enterocytes leads to the development of enteropathy, which closely resembles the lesions in CD patients. Neutralization of IL-15 activity dramatically diminished the pathological changes. Thus, an intervention blocking the activation of CD8 T cells by IL-15 appears to provide an alternative strategy in managing CD to the conventional gluten-free diet.

IL-21

IL-21 is the most recently discovered member of the γc-family. Unlike other family members, IL-21 does not appear to have potent growth-promoting effects. Instead, IL-21 is thought to function more as a differentiation factor than a factor controlling cellular proliferation (See Tagaya, 2010, J. Leuk. Biol. 87:13-15).

Current Strategies for Treating γc-Cytokine-Mediated Disorders

Because the γc-cytokines are thought to be involved in numerous human diseases, several methods of treating γc-cytokine-implicated diseases by inhibiting γc-cytokine family activities have been proposed. These methods include the use of cytokine-specific monoclonal antibodies to neutralize the targeted cytokine's activity in vivo; use of monoclonal antibodies targeting the private cytokine-specific receptor subunits (subunits other than the shared γc-subunit) to selectively inhibit cytokine activity; and use of chemical inhibitors that block the downstream intracellular cytokine signal transduction pathway.

While cytokine-specific antibodies are often the first choice in designing therapeutics, cytokines that share receptor components display overlapping functions (See Paul, W. E., 1989, Cell 57:521-24) and more than one cytokine can co-operate to cause a disease (see example described below). Thus, approaches involving neutralization of a single cytokine may not be effective in the treatment of cytokine-implicated human diseases.

Strategies for designing therapeutics that inhibit the function of multiple cytokines via antibodies which recognize a shared receptor component have also been proposed. However, the multi-subunit nature of cytokine receptor systems and the fact that functional receptors for a single cytokine can assume different configurations makes this approach difficult.

For example, a functional IL-15 receptor can be either IL-15Rβ/γc or IL-15Rα/β/γc. (See Dubois et al., 2002, Immunity 17:537-47.) An antibody against the IL-15Rβ receptor (TMβ1), is an efficient inhibitor of the IL-15 function, but only when the IL-15Rα molecule is absent from the receptor complex. (See Tanaka et al., 1991, J. Immunol. 147:2222-28.) Thus, the effectiveness of a monoclonal anti-receptor antibody, whether raised against a shared or a private subunit, can be context-dependent and is unpredictable in vivo.

Although clinical use of monoclonal antibodies against biologically active factors or receptors associated with the pathogenesis of diseases is an established practice, there are few demonstrations of successful outcomes. Moreover, establishment of a clinically-suited monoclonal antibody treatment is a long and difficult process, with the successful generation of a neutralizing antibody largely a matter of luck. For example, due to the critical importance of the γc-subunit in mediating signaling by γc-family cytokines, many attempts to generate polyclonal and monoclonal antibodies against the γc-subunit have been made and there exist many commercial antibodies recognizing the γc-subunit in mice and in humans. Curiously, however, none of these anti-γc-subunit antibodies block the function of the γc-cytokines.

Another problem with the therapeutic use of monoclonal antibodies is that monoclonal antibodies are usually generated by immunizing rodents with human proteins, so the generated antibody is a foreign protein and thus highly immunogenic. To circumvent this problem, the amino acid sequence of the monoclonal antibody is molecularly modified so that the antibody molecule is recognized as a human immunoglobulin (a process called humanization), but this process requires time and expense.

Targeting JAK3, as an Existing Alternative Example for the Inhibition of Multiple γc-Cytokines The interaction between the γc-subunit and a γc-cytokine leads to the activation of an intracellular protein tyrosine kinase called Janus kinase 3 (Jak3). Jak3, in turn, phosphorylates multiple signaling molecules including STAT5, and PI3 kinase. The interaction of the γc-subunit and Jak3 is very specific. In fact, there is no other receptor molecule that recruits Jak3 for signal transduction. (See O'Shea, 2004, Ann. Rheum. Dis. 63: (suppl. II):ii67-7.) Thus, the inhibition of cytokine signaling through the γc-subunit can be accomplished by blocking the activity of Jak3 kinase. Accordingly, multiple chemical inhibitors that target the kinase activity of Jak3 have been introduced to the market. (See Pesu et al., 2008, Immunol. Rev. 223:132-142.) One such example is CP690,550.

The major shortcoming of these protein kinase inhibitors is the lack of specificity to Jak3 kinase. These drugs intercept the binding of ATP (adenosine-triphosphate) molecules to Jak3 kinase, a common biochemical reaction for many protein kinases, and thus tend to block the action of multiple intracellular protein kinases that are unrelated to Jak3 kinase whose actions are critically needed for the well-being of normal cells in various tissues. Thus, more specific inhibitors of signaling through the γc-subunit are needed.

There is therefore a great need for an alternative strategy for treating γc-cytokine-implicated diseases.

Discovery of the γc-Box

The C-terminus (the D-helix) of the γc-cytokines contains the proposed site for interacting with the common γc-subunit of the multi-unit cytokine receptors. (Bernard et al., 2004 J. Biol. Chem. 279:24313-21.) Comparison of the biochemical properties of the amino acids of all γc-cytokines identified in mice and humans revealed that the chemical nature of the amino acids, for example, hydrophobicity, hydrophilicity, base/acidic nature, are conserved, if not identical, at many positions in the D-helix across the members of the γc-cytokine family.

In contrast, the sequence of IL-13, which is related to the γc-cytokine, IL-4, but does not bind to the γc-subunit, does not exhibit significant homology in the D-helix region to the γc-cytokines, suggesting that the sequence homology in the D-helix region is correlated with binding to the γc-subunit. As shown in FIG. 1A, alignment of the amino acid sequences of the D-helix region of γc-cytokine family members in humans reveals a motif of moderate sequence homology in these cytokines referred to herein as "the γc-box".

The γc-box (SEQ ID NO: 10) comprises 19 amino acids where out of the 19 positions, positions 4, 5, and 13 are fully conserved as Phenylalanine, Leucine, and Glutamine, respectively. Less conservation is observed at positions 6, 7 and 11 of the γc-box where the amino acid is one of two or three related amino acids that share physico-chemical properties: position 6 may be occupied by the polar amino acids Glutamate, Asparagine or Glutamine; non-polar amino acids Serine or Arginine can occupy position 7; and position 11 is occupied by either of the non-polar aliphatic amino acids Leucine or Isoleucine. Positions 9 and 16 may be occupied by the either the non-polar amino acid Isoleucine or the polar amino acid Lysine. See FIG. 1B. Some differences in the amino acid composition of the γc-box are observed at positions 9 and 16 amongst subfamilies of the γc-cytokines.

Comparison of the γc-cytokines across species indicates that Isoleucine is often present at the 9 and 16 positions in the IL-2/15 subfamily, whereas the other γc-family members often possess Lysine in these positions. Not wishing to be bound by a particular theory, Isoleucine and Lysine are biochemically different and thus may impart specific conformational differences between the IL-2/15 subfamily and other γc-cytokines.

Conservation of the γc-box motif between γc-cytokines is supported by findings that an Glutamine (Gln, Q) residue located in the D-helix region is critical for the binding of the γc-cytokines to the γc-subunit. (Bernard et al., 2004 J. Biol. Chem. 279: 24313-21.)

Peptide Inhibitors of γc-Cytokine Activity

The activity of γc-family cytokines may be blocked by disrupting the interaction between the γc-cytokine and the γc-subunit, for example by introducing a competitive inhibitor which can interact with the γc-subunit without stimulating signaling through the multi-subunit cytokine receptors. Not to be bound by a particular theory, the conserved γc-box motif, which participates in binding of the γc-family cytokines to the γc-subunit, presents a core base amino acid sequence which can be utilized to design peptide inhibitors of γc-cytokine signaling.

The core γc-box amino acid sequence comprises: D/E-F-L-E/Q/N-S/R-X-I/K-X-L/I-X-Q (SEQ ID NO: 2) (where X denotes any amino acid). At least some embodiments described herein relate to custom peptide derivatives of the core γc-box amino acid sequence which can inhibit the activity of one or more γc-cytokines. Custom peptide derivatives include any peptide whose partial amino acid sequence shows approximately 50%, 50-60%, 60-70%, 70-80%, 80%, 90%, 95%, 97%, 98%, 99% or 99.8% identity to the core γc-box amino acid sequence. Custom peptide derivatives further include any peptide wherein a partial amino acid sequence of that peptide derivative comprises amino acids with similar physico-chemical properties to the amino acids of the core γc-box. For example, amino acids with similar physico-chemical properties would include Phenylalanine, Tyrosine, Tryptophan, and Histidine, which are aromatic amino acids. FIG. 2 shows a diagrammed representation of amino acids with similar physico-chemical properties which may be may be substituted for the amino acids comprising the core γc-box. Peptide derivatives of the core γc-box may be 11, 12, 13, 14, 15, 16, 17, 18, 19, 20, 21, 22, 24, 25-30, 30-35, 35-40, 40-45, 45-50, or more than 50 amino acids in length. In some embodiments, the custom peptide derivatives may be conjugated to the N-termini, C-termini and/or to the side residues of existing biological proteins/peptides.

Based on the identification of the conserved γc-box motif in cytokines which bind to the γc-subunit, Applicants have devised a novel, 19-mer custom derivative peptide which is an artificial composite peptide combining the amino acid sequence of the human IL-2 and IL-15 γc-box. The 19-mer peptide, herein referred to as BNZ-γ, consists of the amino acid sequence: I-K-E-F-L-Q-R-F-I-H-I-V-Q-S-I-I-N-T-S (SEQ ID NO: 1), where the amino acids depicted by bold characters are conserved between IL-2 and IL-15 and the underlined amino acids represent positions where the physico-chemical properties of the amino acids are conserved.

Applicants discovered that the 19-mer BNZ-γ, suppresses IL-15 and IL-9 induced cellular proliferation, but not IL-3 or IL-4 induced cellular proliferation. See FIG. 3A and EXAMPLE 2. Applicants further demonstrated that BNZ-γ inhibits IL-15 mediated phosphorylation of the intracellular cytokine signal transduction molecule, STAT-5. See FIG. 3C and EXAMPLE 5. These results demonstrate that custom peptide derivatives of the conserved γc-box motif can inhibit the activity of multiple γc-cytokines.

Several embodiments relate to custom derivative peptides of the 19-mer BNZ-γ amino acid sequence, I-K-E-F-L-Q-R-F-I-H-I-V-Q-S-I-I-N-T-S (SEQ ID NO: 1), which can inhibit the activity of one or more γc-cytokines. Custom peptide derivatives of the 19-mer BNZ-γ amino acid sequence include any peptide whose partial amino acid sequence shows approximately 50%, 50-60%, 60-70%, 70-80%, 80%, 90%, 95%, 97%, 98%, 99% or 99.8% identity to amino acid sequence: I-K-E-F-L-Q-R-F-I-H-I-V-Q-S-I-I-N-T-S (SEQ ID NO: 1). Custom peptide derivatives further include any peptide wherein a partial amino acid sequence of that peptide derivative comprises amino acids with similar physico-chemical properties to the amino acids of sequence: I-K-E-F-L-Q-R-F-I-H-I-V-Q-S-I-I-N-T-S (SEQ ID NO: 1). In several embodiments, the amino acid residues of the custom derivative peptides retain similar physico-chemical properties with the amino acid residues of BNZ-γ, but exhibit different biological inhibition specificity to the 6 γc-cytokine family members from that of the original 19-mer peptide. Peptide derivatives of BNZ-γ may be 19, 20, 21, 22, 24, 25-30, 30-35, 35-40, 40-45, 45-50, or more than 50 amino acids in length. In some embodiments, the custom peptide derivatives may be conjugated to the N-termini, C-termini and/or to the side residues of existing biological proteins/peptides.

Several embodiments relate to custom peptide derivatives of the γc-box motifs of IL-15, IL-2, IL-21, IL-4, IL-9, or IL-7, which are depicted in FIG. 1A. Other embodiments relate to custom derivative peptides which are artificial composite peptides combining the amino acid sequence of two or more of the human IL-15, IL-2, IL-21, IL-4, IL-9, and IL-7 γc-box motifs. Several embodiments relate to custom peptide derivatives of the of the γc-box motifs of IL-15, IL-2, IL-21, IL-4, IL-9, or IL-7 having a partial amino acid sequence that shows approximately 50%, 50-60%, 60-70%, 70-80%, 80%, 90%, 95%, 97%, 98%, 99% or 99.8% identity to amino acid sequences of the of the γc-box motifs of IL-15, IL-2, IL-21, IL-4, IL-9, or IL-7. Custom peptide derivatives of the of the γc-box motifs of IL-15, IL-2, IL-21, IL-4, IL-9, or IL-7 further include any peptide wherein a partial amino acid sequence of that peptide derivative comprises amino acids with similar physico-chemical properties to the amino acids of sequence of the γc-box motifs of IL-15, IL-2, IL-21, IL-4, IL-9, or IL-7.

Several embodiments relate to custom peptide derivatives that would inhibit the function of one, all, or selective members of the γc-cytokines. In some embodiments, the custom peptide derivatives selectively target individual γc-cytokine family members. For example, a custom peptide derivative can selectively inhibit the function of IL-2, IL-4, IL-7, IL-9, IL-15, or IL-21. In other embodiments, a custom peptide derivative can inhibit 2 or more γc-cytokine family members.

For example, the custom peptide derivatives of the present embodiments can selectively inhibit the function of IL-2 in combination with one or more of IL-4, IL-7, IL-9, IL-15, and IL-21; IL-4 in combination with one or more of IL-7, IL-9, IL-15, and IL-21; IL-7 in combination with one or more of IL-9, IL-15, and IL-21; IL-9 in combination with one or more of IL-2, IL-4, IL-7, IL-15, and IL-21; IL-15 in combination with one or more of IL-2, IL-4, IL-7, IL-9, and IL-21; or IL-21 in combination with one or more of IL-2, IL-4, IL-7, IL-9, and IL-15. In other embodiments, custom peptide derivatives can comprehensively target all γc-cytokine family members.

Not wishing to be bound by a particular theory, the custom peptide derivatives can inhibit the function of all or selective members of the γc-cytokines by diminishing the binding of γc-cytokines to the γc-subunit, for example, as a competitive inhibitor. Such custom peptide derivatives may be used in diverse applications, including as a clinical drug.

Several embodiments relate to custom peptide derivatives that would modulate (including enhance or reduce) the function of one, two, or more of selective members of the γc-cytokines. In some embodiments, the custom peptide derivatives selectively target individual γc-cytokine family members. For example, a custom peptide derivative can selectively enhance or inhibit the function of IL-2, IL-4, IL-7, IL-9, IL-15, or IL-21. In other embodiments, a custom peptide derivative can enhance or inhibit two or more γc-cytokine family members. In certain embodiments, custom peptide derivatives may comprise P-K-E-F-L-E-R-F-V-H-L-V-Q-M-F-I-H-Q-S-L-S (SEQ ID NO: 3), which can enhance or inhibit the activity of one, two or more of γc-cytokines. In certain embodiments, custom peptide derivatives may comprise P-K-E-F-L-E-R-F-V-H-L-V-Q-M-F-I-H-Q-S-L-S (SEQ ID NO: 3), which can inhibit the activity of at least IL-15 and IL-21.

In some embodiments, custom peptide derivatives may include any peptide whose partial amino acid sequence shows approximately 50%, 50-60%, 60-70%, 70-80%, 80%, 90%, 95%, 97%, 98%, 99% or 99.8% identity to amino acid sequence: P-K-E-F-L-E-R-F-V-H-L-V-Q-M-F-I-H-Q-S-L-S (SEQ ID NO: 3). Custom peptide derivatives further include any peptide wherein a partial amino acid sequence of that peptide derivative comprises amino acids with similar physico-chemical properties to the amino acids of sequence: P-K E F L E R F V H-L-V-Q-M-F-I-H-Q-S-L-S (SEQ ID NO: 3).

In several embodiments, the amino acid residues of the custom derivative peptides retain similar physico-chemical properties with the amino acid residues of P-K-E-F-L-E-R-F-V-H-L-V-Q-M-F-I-H-Q-S-L-S (SEQ ID NO: 3), but exhibit different biological inhibition specificity to the 6 γc-cytokine family members (i.e. IL-2, IL-4, IL-7, IL-9, IL-15, or IL-21) from that of the original peptide of P-K-E-F-L-E-R-F-V-H-L-V-Q-M-F-I-H-Q-S-L-S (SEQ ID NO: 3). Peptide derivatives of the sequence of P-K-E-F-L-E-R-F-V-H-L-V-Q-M-F-I-H-Q-S-L-S (SEQ ID NO: 3) may be 19, 20, 21, 22, 24, 25-30, 30-35, 35-40, 40-45, 45-50, or more than 50 amino acids in length.

In some embodiments, the custom peptide derivatives may be conjugated to the N-termini, C-termini and/or to the side residues of existing biological proteins/peptides. In some embodiments, the composite peptide of SEQ ID NO: 3 may be conjugated to other moieties through the N-terminus, C-terminous or side chains of the composite peptide. The other moieties may include proteins or peptides that stabilize the composite peptide, or other moieties, including without limitation, bovine serum albumin (BSA), albumin, Keyhold Limpet Hemocyanin (KLH), Fc region of IgG, a biological protein that functions as scaffold, an antibody against a cell-specific antigen, a receptor, a ligand, a metal ion and Poly Ethylene Glycol (PEG).

The terms "oligopeptide," "polypeptide," "peptide," and "protein" can be used interchangeably when referring to the custom peptide derivatives provided in accordance with the present embodiments and can be used to designate a series of amino acid residues of any length. Peptides according to the present embodiments may also contain non-natural amino acids. Linker elements can be joined to the peptides of the present embodiments through peptide bonds or via chemical bonds. The peptides of the present embodiments may be linear or cyclic, and may include (D) as well as (L) amino acids.

Peptides of the present embodiments may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylamino), with or without any of a wide variety of side chain modifications and/or substitutions (e.g., methylation, benzylation, t-butylation, tosylation, alkoxycarbonylamino, and the like).

Residues other than common amino acids that may be present include, but are not limited to, penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoadipic acid, m-aminomethylbenzoic acid, and diaminopropionic acid.

Peptides of the present embodiments can be produced and obtained by various methods known to those skilled in the art. For example, the peptide may be produced by genetic engineering, based on the nucleotide sequence coding for the peptide of the present embodiments, or chemically synthesized by means of peptide solid-phase synthesis and the like, or produced and obtained in their combination.

One skilled in the art can synthesize the custom peptide derivatives based on the present disclosure of the conserved γc-box motif and knowledge of the biochemical properties of amino acids as described in FIG. 2. Some embodiments also relate to polynucleotides comprising nucleotide sequences encoding the peptides of the present invention. "Nucleotide sequence," "polynucleotide," or "nucleic acid" can be used interchangeably, and are understood to mean either double-stranded DNA, a single-stranded DNA or products of transcription of the said DNAs (e.g., RNA molecules). Polynucleotides can be administered to cells or subjects and expressed by the cells or subjects, rather than administering the peptides themselves. Several embodiments also relate to genetic constructs comprising a polynucleotide sequence encoding the peptides of the present invention. Genetic constructs can also contain additional regulatory elements such as promoters and enhancers and, optionally, selectable markers.

Methods of Treating γc-Cytokine Mediated Diseases

Several embodiments relate to the use of γc-antagonist peptides in the treatment of γc-cytokine mediated diseases. Use of custom peptide derivative according to the present embodiments allows for flexibility in the design of the therapeutic agent (custom design of the peptide) and enables more comprehensive outcomes, which would not be accomplished by conventional strategies employing anti-cytokine or anti-cytokine receptor antibodies.

Described herein is a novel method of blocking the action of γc-family cytokines. Such manipulations can yield effective methods of clinical interventions in treating diseases related to the dysregulation or dysfunction of γc-cytokines. Examples of disease that may be treated by disrupting the interaction between the γc-cytokine and the γc-subunit include autoimmune diseases such as systemic lupus erythematosis, Sjögren's syndrome, Wegener's granulomatosis Celiac disease, Hashimoto's or auto-immune thyroiditis;

collagen diseases including rheumatoid arthritis, inflammatory bowel disease, diabetes mellitus, autoimmune diseases of the skin such as psoriasis; degenerative neuronal diseases such as multiple sclerosis, uvietis or inflammation of the eye and sympathetic ophthalmia, graft-versus-host disease (GvHD) and myasthenia gravis.

In some embodiments, the γc-antagonist peptides described herein may be used in the treatment of 1-Human T-cell Lymphotropic type I and II (HTLV-I and HTLV-II)-associated diseases including Adult T-cell Leukemia (ATL), HTLV-associated Myelopathy/Tropical Spastic Paraparesis (HAM/TSP), and other non-neoplastic inflammatory diseases associated with HTLV such as uveitis (HU), arthropathy, pneumopathy, dermatitis, exocrinopathy and myositis. In some embodiments, the γc-antagonist peptides described herein may be used in the treatment of other viral diseases such as influenza, AIDS, HBV and Herpes or parasitic diseases.

In several embodiments, the γc-antagonist peptides may be administered before, during, and or after transplantation of various organs as an immunosuppressant agent.

In some embodiments, the γc-antagonist peptides described herein may be used in the treatment of immune-mediated diseases such as asthma and other inflammatory respiratory diseases, such as, but not limited to sinusitis, hay fever, bronchitis, chronic obstructive pulmonary disease (COPD), allergic rhinitis, acute and chronic otitis, lung fibrosis. In some embodiments, γc-antagonist peptides may be administered to treat or prevent allergic reactions due to exposure to allergens, chemical agents or other common causes of acute respiratory disease. In some embodiments, γc-antagonist peptides may be administered to treat or prevent inflammatory responses caused by viruses, bacteria, chemical reagents, and biochemical reagents.

In several embodiments, the γc-antagonist peptides may be administered to treat some types of malignancies such as LGL-leukemia, Intraepithelial lymphoma and leukemia in Refractory Celiac Disease, NK leukemia/lymphoma and NK-T leukemia/lymphoma In some embodiments, custom peptide derivatives according to the embodiments described herein can be used for cosmetic purposes, such as the treatment of acne, hair loss, sunburn and nail maintenance, included to ointment as anti-aging component because of the anti-inflammatory nature of them.

Several embodiments relate to therapeutic antagonist peptides that would inhibit the function of all or selective members of the γc-cytokines. In some embodiments, therapeutic antagonist peptides selectively inhibit individual γc-cytokine family members (custom peptides). In other embodiments, therapeutic antagonist peptides can comprehensively inhibit all γc-cytokine family members (Simul-Block). In some embodiments, therapeutic antagonist peptides selectively inhibit subsets of the γc-cytokines. Not wishing to be bound by a particular theory, the peptide antagonists can inhibit the function of all or selective members of the γc-cytokines by diminishing the binding of γc-cytokines to the γc-subunit, for example, as a competitive inhibitor.

Several members of the γc-cytokine family, IL-2, IL-7, and IL-15, but not IL-4 have been implicated as being involved in graft versus host disease (GvHD) in an experimental mouse model. (Miyagawa et al., 2008 J. Immunol. 181:1109-19.) One embodiment relates to the use of therapeutic antagonist peptides that selectively inhibit IL-2, IL-7, and IL-15 activity for the treatment of GvHD in humans, allowing survival of the grafted tissues or bone marrow cells. Other embodiments relate to the use of therapeutic antagonist peptides that selectively inhibit a combination of IL-2 and IL-7, IL-2, and IL-15, or IL-7 and IL-15 to treat GvHD. Other embodiments relate to the use of a combination of therapeutic antagonist peptides that selectively inhibit IL-2, IL-7, or IL-15.

Some embodiments relate to the use of therapeutic antagonist peptides that selectively inhibit IL-2 function for the treatment of autoimmune disorders where T-regs have been implicated as playing a role. In some embodiments, peptide-mediated inhibition of T-regs can enhance the natural anti-cancer immunity in humans, providing a novel means of anti-cancer therapy.

Several embodiments relate to the use of therapeutic antagonist peptides that selectively inhibit IL-4 to treat asthma.

Some embodiments relate to the use of therapeutic antagonist peptides that selectively inhibit IL-7 either alone or in combination with therapeutic antagonist peptides that selectively inhibit the γc-cytokine family member, IL-15, as a therapeutic agent for LGL leukemia. In some embodiments therapeutic antagonist peptides that selectively inhibit both IL-7 and IL-15 activity can be used to treat LGL leukemia. Several embodiments relate to the use of BNZ-γ to treat LGL leukemia. In some embodiments, specific γc-antagonist peptides that selectively IL-15 alone or specific γc-antagonist peptides that selectively IL-15 and IL-7 are used as a therapeutic agent for CD4/CD8 T lymphocyte-associated leukemia including that caused by the HTLV-I.

Several embodiments relate to the use of γc-antagonist peptides that selectively inhibit the activity of IL-9, either alone or in combination with the other γc-cytokine family members, as a therapeutic agent for human diseases that involve the abnormal development of Th17 cells.

Several embodiments relate to the use of therapeutic antagonist peptides that selectively inhibit IL-15 activity as a therapeutic agent for treating CD. One recent publication suggested that IL-21, in addition to IL-15, may play a role in CD pathogenesis. (See Bodd et al., 2010, Mucosal Immunol. 3:594-601.) This suggests that optimum treatment of CD by conventional anti-cytokine or cytokine-receptor antibodies would benefit from a combination of at least two antibodies recognizing component that belong to the IL-15 and IL-21 systems. In some embodiments, custom derivative antagonist peptides that selectively inhibit both IL-15 and IL-21 activity are used as a therapeutic agent for treating CD.

In addition to having therapeutic applications, γc-antagonist peptides have applications in consumer products as well. Several embodiments relate to the use of γc-antagonist peptides in skin care products such as anti-aging, anti-inflammatory, anti-acne, and other related applications. Some embodiments relate to the use of γc-antagonist peptides in hair products as anti-hair loss ingredient to treat hair loss caused by autoimmune disorders.

Another embodiment relates to the development of chemical compounds (non-peptide, non-protein) that have a spatial structure which resembles the 19-mer amino acid sequence I-K-E-F-L-Q-R-F-I-H-I-V-Q-S-I-I-N-T-S (SEQ ID NO: 1) and can fit into the pocket of the γc-subunit to structurally hinder the access of a γc-cytokine to the γc-subunit for binding. Some embodiments relate to the use of structurally similar chemical compounds as inhibitors of γc-cytokine activity. Such molecular mimicry strategy to further refine the development of synthetic compounds resembling in structure to existing biological peptide/proteins is described in Orzaez et al., 2009 Chem. Med. Chem.

4:146-160. Another embodiment relates to administration of chemical compounds (non-peptide, non-protein) that have a resembling 3D structure as the 19-mer amino acids sequence I-K-E-F-L-Q-R-F-I-H-I-V-Q-S-I-I-N-T-S (SEQ ID NO: 1) to treat γc-cytokine-mediated diseases.

Several embodiments relates to the administration of a peptide of amino acid sequence I-K-E-F-L-Q-R-F-I-H-I-V-Q-S-I-I-N-T-S (SEQ ID NO: 1) to treat γc-cytokine-mediated diseases. Another embodiment relates to the administration of derivative peptides of amino acid sequence I-K-E-F-L-Q-R-F-I-H-I-V-Q-S-I-I-N-T-S (SEQ ID NO: 1), wherein the amino acid sequence of the derivative peptide has similar physico-chemical properties as a peptide of the amino acid sequence I-K-E-F-L-Q-R-F-I-H-I-V-Q-S-I-I-N-T-S (SEQ ID NO: 1), but has distinct biological activity, to treat γc-cytokine-mediated diseases. Another embodiment relates to administration of a peptide of amino acid sequence I-K-E-F-L-Q-R-F-I-H-I-V-Q-S-I-I-N-T-S (SEQ ID NO: 1) conjugated to the N- and C-termini or to the side residues of existing biological proteins/peptides into patients to treat γc-cytokine-mediated diseases.

Several embodiments relate to administration of polyclonal and monoclonal antibodies raised against a peptide comprising of amino acid sequence I-K-E-F-L-Q-R-F-I-H-I-V-Q-S-I-I-N-T-S (SEQ ID NO: 1) into patients as an immunogen to treat γc-cytokine-mediated diseases. Another embodiment relates to administration of polyclonal and monoclonal antibodies that were raised against derivative peptides of amino acid sequence I-K-E-F-L-Q-R-F-I-H-I-V-Q-S-I-I-N-T-S (SEQ ID NO: 1) wherein the amino acid sequence of the derivative peptide has similar physico-chemical properties as a peptide of the amino acid sequence I-K-E-F-L-Q-R-F-I-H-I-V-Q-S-I-I-N-T-S (SEQ ID NO: 1), but has distinct biological activity, into patients as an immunogen to treat γc-cytokine-mediated diseases.

Administration of γc-Antagonist Peptides

The present embodiments also encompass the use of γc-antagonist peptides for the manufacture of a medicament for the treatment of a disease. The present embodiments also encompass a pharmaceutical composition that includes γc-antagonist peptides in combination with a pharmaceutically acceptable carrier. The pharmaceutical composition can include a pharmaceutically acceptable carrier and a non-toxic therapeutically effective amount of γc-antagonist peptides, or other compositions of the present embodiments.

The present embodiments provide methods of using pharmaceutical compositions comprising an effective amount of antagonists for γc-cytokines in a suitable diluent or carrier. A γc-antagonist of the present embodiments can be formulated according to known methods used to prepare pharmaceutically useful compositions. A γc-antagonist can be combined in admixture, either as the sole active material or with other known active materials, with pharmaceutically suitable diluents (e.g., phosphate, acetate, Tris-HCl), preservatives (e.g., thimerosal, benzyl alcohol, parabens), emulsifying compounds, solubilizers, adjuvants, and/or carriers such as bovine serum albumin.

Suitable carriers and their formulations are described in Remington's Pharmaceutical Sciences, 16$^{th}$ ed. 1980 Mack Publishing CO. Additionally, such compositions can contain a γc-antagonist complexed with polyethylene glycol (PEG), metal ions, or incorporated into polymeric compounds such as polyacetic acid, polyglycolic acid, hydrogels etc., or incorporated into liposomes, microemulsions, micelles, unilamellar or multilamellar vesicles, erythrocyte ghosts, or spheroblasts. Such compositions will influence the physical state, solubility, stability, rate of in vivo release, and rate of in vivo clearance or a γc-antagonist. A γc-antagonist can be conjugated to antibodies against cell-specific antigens, receptors, ligands, or coupled to ligands for tissue-specific receptors.

Methods of administrating γc-antagonists of the present embodiments may be selected as appropriate, depending on factors, such as the type of diseases, the condition of subjects, and/or the site to be targeted. The γc-antagonists can be administered topically, orally, parenterally, rectally, or by inhalation. The term "parenteral" includes subcutaneous injections, intravenous, intramuscular, intraperitoneal, intracisternal injection, or infusion techniques. These compositions will typically include an effective amount of a γc-antagonist, alone or in combination with an effective amount of any other active material.

The amount of the peptide contained in pharmaceutical compositions of the present embodiments, dosage form of the pharmaceutical compositions, frequency of administration, and the like may be selected as appropriate, depending on factors, such as the type of diseases, the condition of subjects, and/or the site to be targeted. Such dosages and desired drug concentrations contained in the compositions may vary affected by many parameters, including the intended use, patient's body weight and age, and the route of administration. Pilot studies will first be conducted using animal studies and the scaling to human administration will be performed according to art-accepted practice.

In one embodiment, host cells that have been genetically modified with a polynucleotide encoding at least one γc-antagonist peptide are administered to a subject to treat a proliferation disorder and/or to reduce the growth of malignant cells. The polynucleotide is expressed by the host cells, thereby producing the peptides within the subject. Preferably, the host cells are allogeneic or autogeneic to the subject.

In a further aspect, γc-antagonist peptides can be used in combination with other therapies, for example, therapies inhibiting cancer cell proliferation and growth. The phrase "combination therapy" embraces the administration of γc-antagonist peptides and an additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected).

A combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by an appropriate route including, but not limited to, oral routes, intravenous routes, intramuscular routes, and direct absorption through mucous membrane tissues. There therapeutic agents can be administered by the same route or by different routes. The sequence in which the therapeutic agents are administered is not narrowly critical.

Combination therapy also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporarily removed from the administration of the therapeutic agents, perhaps by days or even weeks.

In certain embodiments, γc-antagonist peptides can be administered in combination with at least one anti-proliferative agent selected from the group consisting of chemotherapeutic agent, an antimetabolite, and antitumorgenic agent, and antimitotic agent, and antiviral agent, and antineoplastic agent, an immunotherapeutic agent, and a radiotherapeutic agent.

In certain embodiments, γc-antagonist peptides can be administered in combination with at least one anti-inflammatory agent selected from the group consisting of steroids, corticosteroids, and nonsteroidal anti-inflammatory drugs.

Also provided are kits for performing any of the methods provided herein. In some embodiments, kits may include one or more γc-antagonist according to any of the embodiments provided herein. In some embodiments, the kit may include instructions. Instructions may be in written or pictograph form, or may be on recorded media including audio tape, audio CD, video tape, DVD, CD-ROM, or the like. The kits may comprise packaging.

Definitions

As used herein, the term "patient" refers to the recipient of a therapeutic treatment and includes all organisms within the kingdom animalia. In preferred embodiments, the animal is within the family of mammals, such as humans, bovine, ovine, porcine, feline, buffalo, canine, goat, equine, donkey, deer, and primates. The most preferred animal is human.

As used herein, the term "treat" or any variation thereof (e.g., treatment, treating, etc.), refers to any treatment of a patient diagnosed with a biological condition, such as CD4−, CD8−, and LGL-leukemia, an autoimmune disease, systemic lupus erythematosis, Sjögren's syndrome, Wegener's granulomatosis, Celiac disease, Hashimoto's thyroiditis, a collagen disease, rheumatoid arthritis, inflammatory bowel disease, diabetes mellitus, psoriasis, a degenerative neuronal disease, multiple sclerosis, uvietis, inflammation of the eye, graft-versus-host disease (GvHD), myasthenia gravis, 1-Human T-cell Lymphotropic type I and II (HTLV-I and HTLV-II)-associated diseases, Adult T-cell Leukemia (ATL), HTLV-associated Myelopathy/Tropical Spastic Paraparesis (HAM/TSP), uveitis (HU), arthropathy, pneumopathy, dermatitis, exocrinopathy, myositis, influenza, AIDS, HBV, Herpes, asthma, sinusitis, hay fever, bronchitis, chronic obstructive pulmonary disease (COPD), allergic rhinitis, acute and chronic otitis, lung fibrosis, NK leukemia/lymphoma and NK-T leukemia/lymphoma.

The term treat, as used herein, includes: (i) preventing or delaying the presentation of symptoms associated with the biological condition of interest in an at-risk patient who has yet to display symptoms associated with the biological condition; (ii) ameliorating the symptoms associated with the biological condition of interest in a patient diagnosed with the biological condition; (iii) preventing, delaying, or ameliorating the presentation of symptoms associated with complications, conditions, or diseases associated with the biological condition of interest in either an at-risk patient or a patient diagnosed with the biological condition; (iv) slowing, delaying or halting the progression of the biological condition; and/or (v) preventing, delaying, slowing, halting or ameliorating the cellular events of inflammation.

The term "symptom(s)" as used herein, refers to common signs or indications that a patient is suffering from a specific condition or disease.

The term "effective amount," as used herein, refers to the amount necessary to elicit the desired biological response. In accordance with the present embodiments, an effective amount of a γc-antagonist is the amount necessary to provide an observable effect in at least one biological factor for use in treating a biological condition.

"Recombinant DNA technology" or "recombinant" refers to the use of techniques and processes for producing specific polypeptides from microbial (e.g., bacterial, yeast), invertebrate (insect), mammalian cells or organisms (e.g., transgenic animals or plants) that have been transformed or transfected with cloned or synthetic DNA sequences to enable biosynthesis of heterologous peptides. Native glycosylation pattern will only be achieved with mammalian cell expression system. Prokaryotic expression systems lack the ability to add glycosylation to the synthesized proteins. Yeast and insect cells provide a unique glycosylation pattern that may be different from the native pattern.

A "Nucleotide sequence" refers to a polynucleotide in the form of a separate fragment or as a component of a larger DNA construct that has been derived from DNA or RNA isolated at least once in substantially pure form, free of contaminating endogenous materials and in a quantity or concentration enabling identification, manipulation, and recovery of its component nucleotide sequences by standard molecular biology methods (as outlined in Current Protocols in Molecular Biology).

"Recombinant expression vector" refers to a plasmid comprising a transcriptional unit containing an assembly of (1) a genetic element or elements that have a regulatory role in gene expression including promoters and enhances, (2) a structure or coding sequence that encodes the polypeptide according to the present embodiments, and (3) appropriate transcription and translation initiation sequence and, if desired, termination sequences. Structural elements intended for use in yeast and mammalian system preferably include a signal sequence enabling extracellular secretion of translated polypeptides by yeast or mammalian host cells.

"Recombinant microbial expression system" refers to a substantially homogenous monoculture of suitable hot microorganisms, for example, bacteria such as *E. coli*, or yeast such as *S. cerevisiae*, that have stably integrated a recombinant transcriptional unit into chromosomal DNA or carry the recombinant transcriptional unit as a component of a residual plasmid. Generally, host cells constituting a recombinant microbial expression system are the progeny of a single ancestral transformed cell. Recombinant microbial expression systems will express heterologous polypeptides upon induction of the regulatory elements linked to a structural nucleotide sequence to be expressed.

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure.

It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

It should be understood, however, that this detailed description, while indicating preferred embodiments of the invention, is given by way of illustration only, since various changes and modifications within the spirit and scope of the invention will become apparent to those skilled in the art.

EXAMPLES

The following Examples are presented for the purposes of illustration and should not be construed as limitations.

Example 1—Method for Assessing the Inhibitory Activity of γc-Antagonist Peptide

The capacity of any custom derivative peptide prepared according to the present embodiments for inhibiting the action of one γc-cytokine family member is determined using mammalian cellular assays to measure their proliferative response to the γc-cytokine family member.

For each of the six γc-cytokines, indicator cell lines: CTLL-2, a murine CD8 T cells line available from American Type Culture Collection, and PT-18, a murine mast cell line and its subclone PT-18β, is transfected with human IL-2Rβ gene to make the cells responsive to IL-2 and IL-15 (Tagaya et al., 1996, EMBO J. 15:4928-39), and is used to quantitatively determine the γc-cytokine's growth-promoting activity (See Current protocols in Immunology from Wiley and Sons for a methodological reference). The indicator cells demonstrate semi-linear dose-dependent response when measured by a colorimetric WST-1 assay over a range of concentrations (See Clontech PT3946-1 and associated user manual, incorporated herein by reference, for a detailed description of the reagents and methods).

Once the appropriate doses of the cytokine that yield the 50% and 95% maximum response from the indicator cell line is determined, various concentrations (ranging from 1 pM to 10 µM) of the purified or synthesized custom derivative peptide is added to each well containing the cytokine and indicator cells. The reduction in light absorbance at 450 nm is used as an indicator of inhibition of cytokine-stimulated cellular proliferation. Typically, the cells are stimulated by the cytokines such that the absorbance of the well containing indicator cell line and the cytokine is between 2.0 and 3.0, which is reduced to a range of 0.1 to 0.5 by the addition of inhibitory peptides.

Example 2—BNZ-γ Peptide Specifically Inhibits the Growth-Promoting Activities of IL-9 and IL-15

Figure 3A:
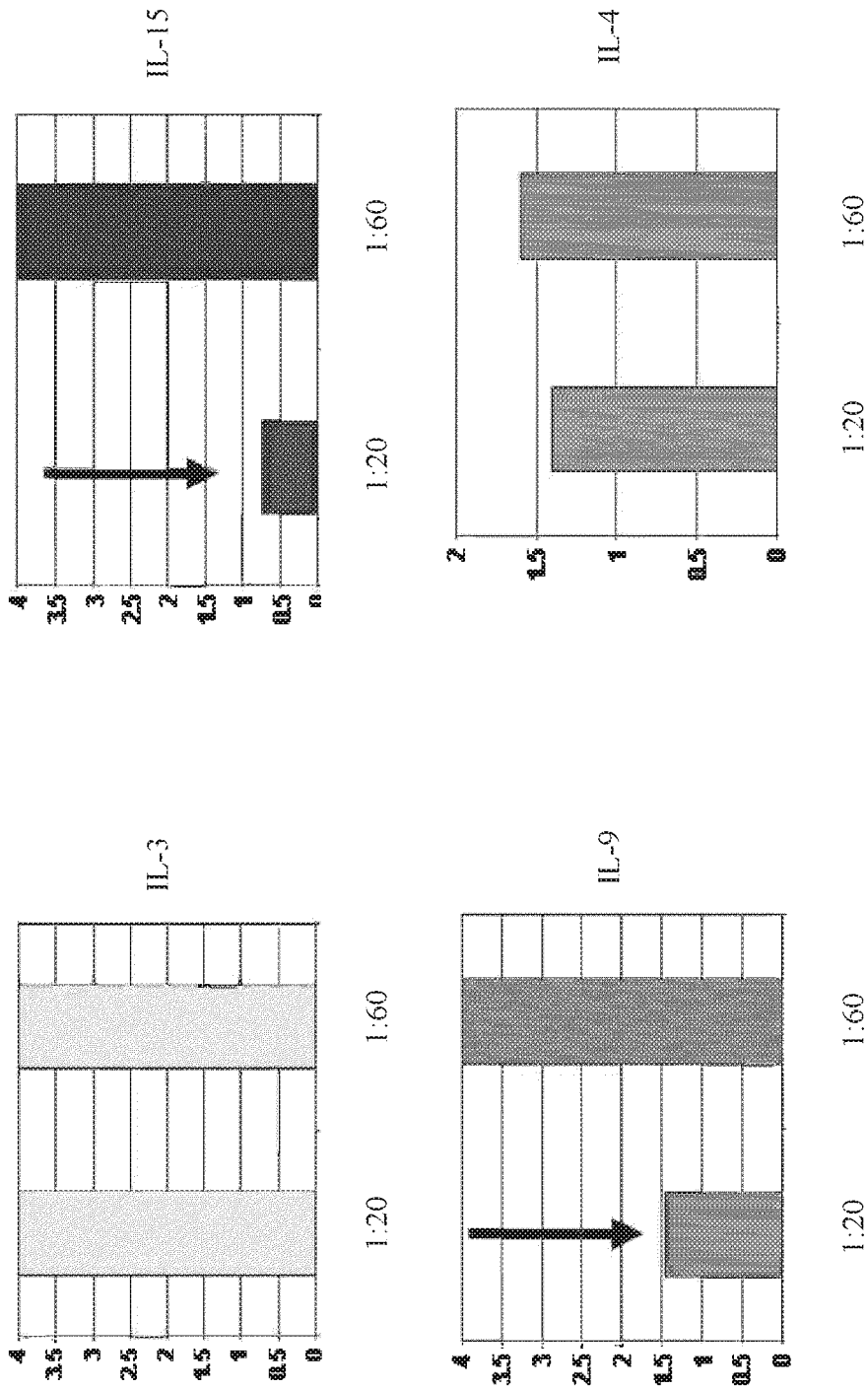
FIG. 3A shows inhibition of IL-15 and IL-9 activity by BNZ-γ in a PT-18 proliferation assay.

Using PT-18β cells as described above, the ability of the BNZ-γ peptide to specifically inhibit the growth-promoting activity of select γc-cytokines was determined (FIG. 3A). IL-3, a non-γc-cytokine that supports the growth of PT-18β cells, was used as a negative control. Briefly, PT-18β cells were incubated either with two different dilutions of BNZ-γ peptide produced by HEK293T cells (1:20 or 1:50 dilution of the original supernatant of HEK293T cells transfected with a BNZ-γ expression construct) or without BNZ-γ peptide in the presence of IL-3, IL-9, IL-15, or IL-4 (1 nM of each cytokine in the culture).

The growth-responses of the cells were determined 2 days after the introduction of BNZ-γ peptide and the cytokine using the WST-1 assay. The growth-promoting activity of IL-3 (a non γc-cytokine) was not inhibited by BNZ-γ. In contrast, the activity of IL-15 and IL-9 were significantly ($p<0.01$ Student's T test) reduced by the BNZ-γ peptide. Cellular proliferation stimulated by IL-4, another γc-cytokine, was not affected by the by the addition of BNZ-γ peptide. Results for IL-3, IL-9, IL-15, and IL-4 are shown at FIG. 3A.

Figure 3B:
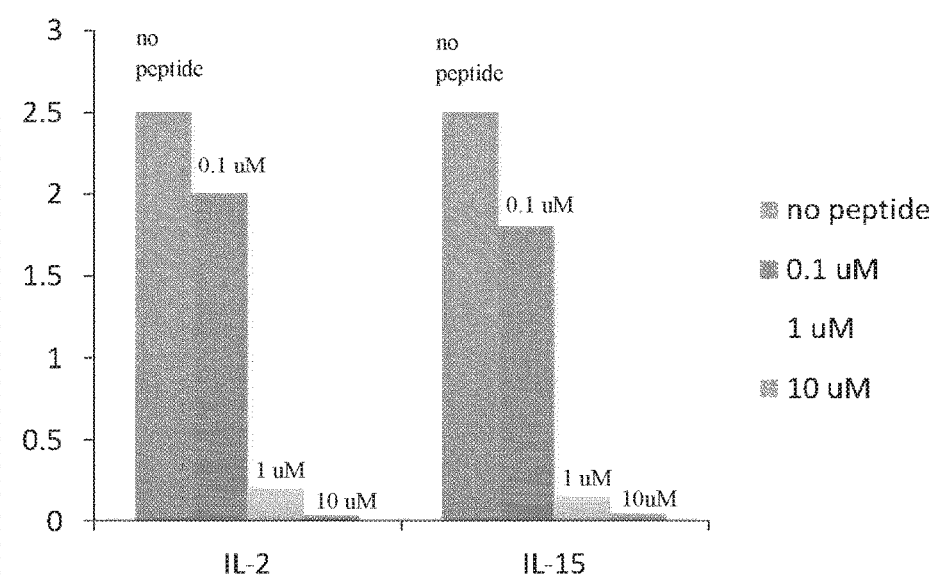
FIG. 3B shows a proliferation assay of CTTL2 cells grown in the presence of IL-2 or IL-15 and 0, 0.1, 1 or 10 uM BNZ-γ.
Figure 3C:
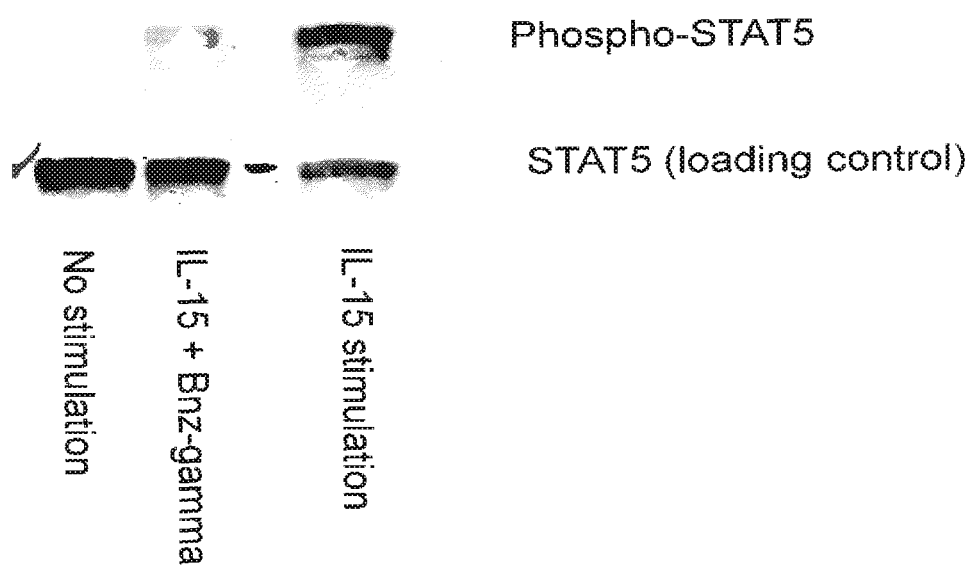
FIG. 3C shows inhibition of IL-15-mediated tyrosine-phosphorylation of STAT5 by BNZ-γ.
Figure 4A:
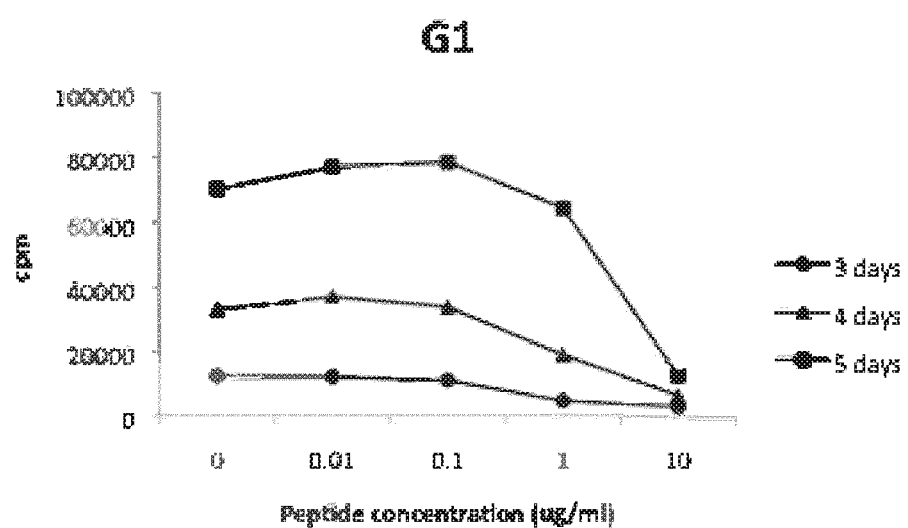
FIG. 4A shows an ex vivo T-cell proliferation assay using HAM/TSP peripheral blood. T-cell proliferation is inhibited by addition of BNZ-γ.
Figure 4B:
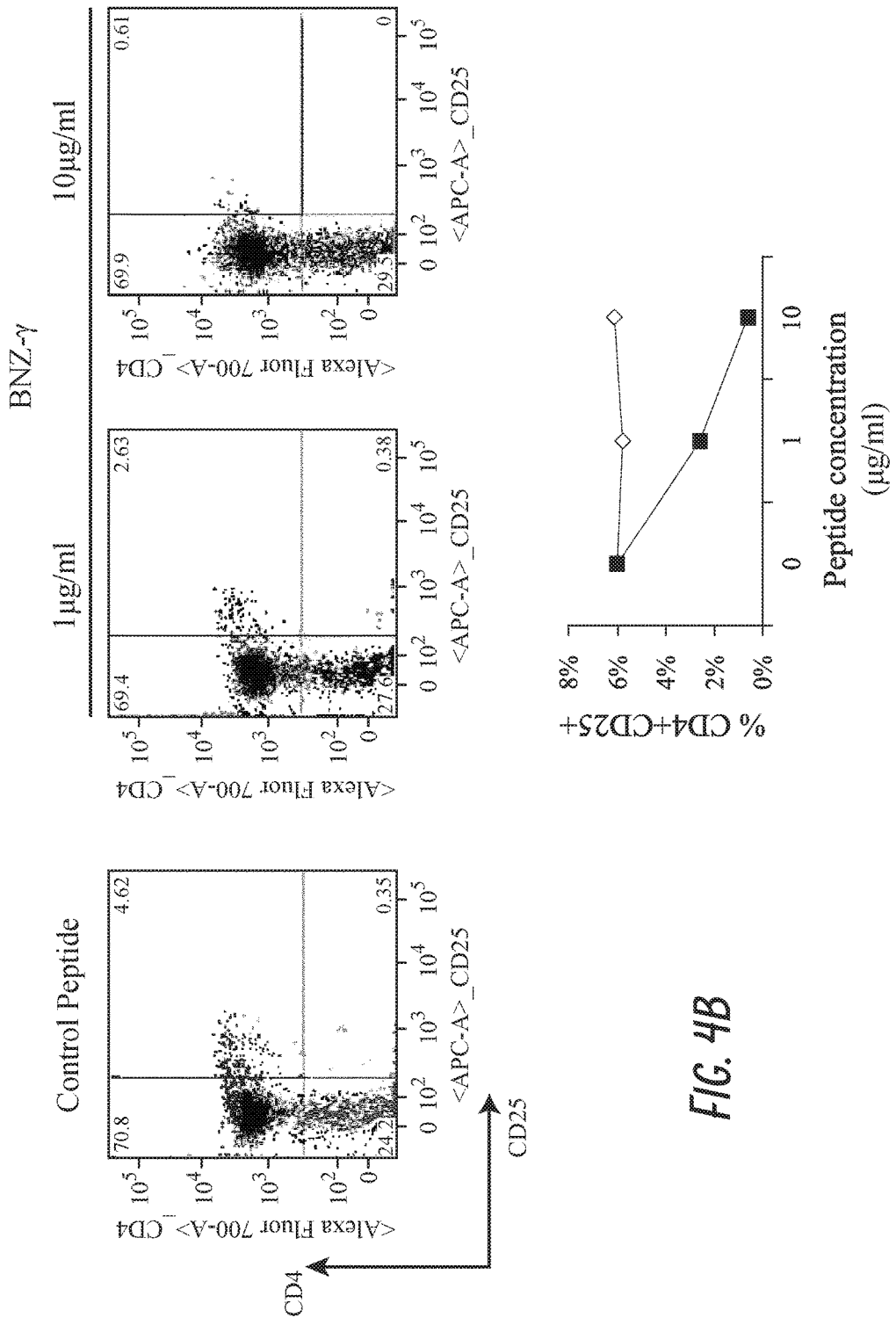
FIG. 4B shows the population of CD4+CD25+ cells in an ex vivo T-cell proliferation assay using HAM/TSP peripheral blood is diminished after adding BNZ-γ to the culture.
Figure 4C:
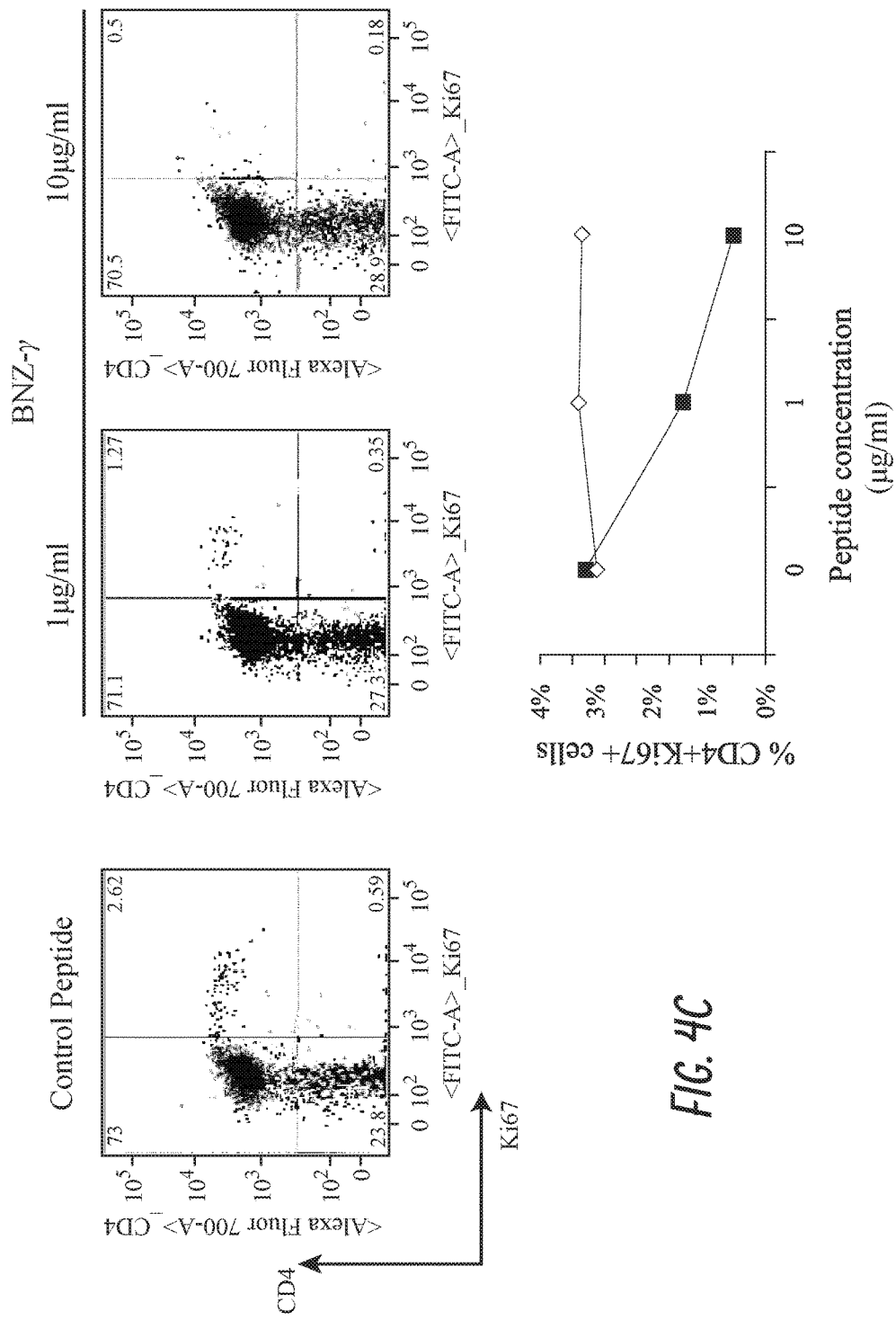
FIG. 4C shows the population of CD4+Ki67 cells in an ex vivo T-cell proliferation assay using HAM/TSP peripheral blood is reduced after adding BNZ-γ to the culture.
Figure 4D:
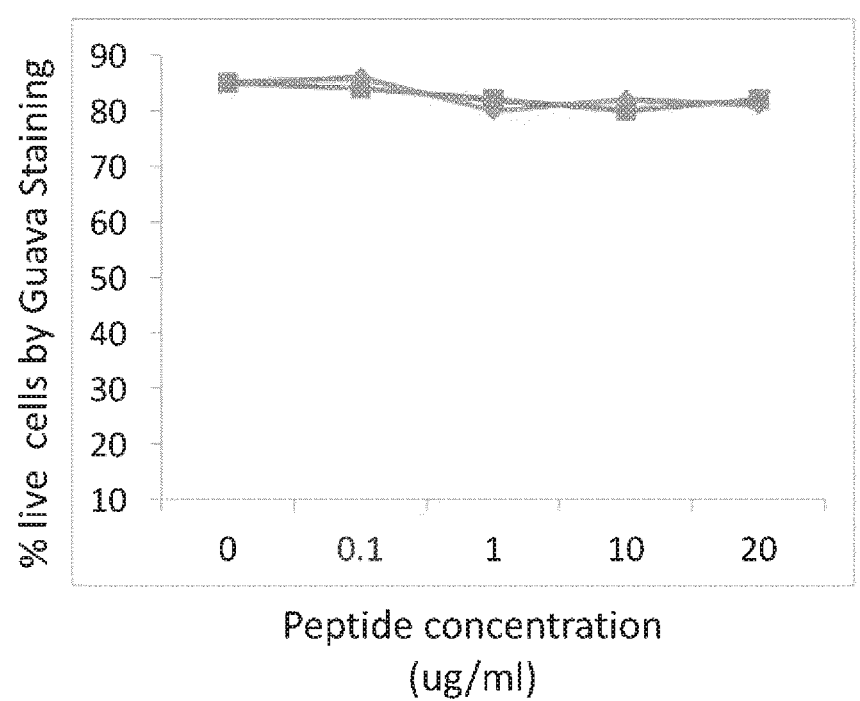
FIG. 4D shows the percent of live cells by Guava staining in an ex vivo T-cell proliferation assay using HAM/TSP peripheral blood is not impacted after adding BNZ-γ to the culture.

In a similar assay, the murine cell line CTTL2 was used. In this assay the cells were cultured with 0.5 nM of recombinant IL-2 in RPMI 10% fetal Calf Serum. To set up the proliferation assay, cells were washed from the cytokines 3 times. Cells were seeded at 1×10(5) cells per well of a 96-well plate with final concentration of 50 pM of IL-2 or IL-15. Various concentration of BNZ-γ peptide (0.1, 1, and 10 ug/ml) was added to each well. Cells were cultured for 20 hours and in the last 4 hours, $^3$H-thymidine was added to the plates. Cells were harvested using a plate reader. The data is shown in FIG. 3B.

Example 3—Method for Measuring Inhibition γc-Cytokine Activity by Assaying 3H-Thymidine Incorporation of as a Marker of Cellular Proliferation Inhibition of γc-cytokine-induced proliferation of an indicator cell population by antagonist custom derivative peptides is measured by the 3H-thymidine incorporation assay. Briefly, radiolabeled thymidine (1 microCi) is given to 20-50,000 cells undergoing proliferation in the presence of cytokines. The cell-incorporated radioactivity is measured by trapping cell-bound radioactivity to a glass-fiber filter using a conventional harvester machines (for example, Filtermate Universal Harvester from Perkin-Elmer), after which the radioactivity is measured using a b-counter (for example, 1450 Trilux microplate scintillation counter).

Example 4—Method for Measuring Inhibition γc-Cytokine Activity by Assaying Incorporation of a Cell-Tracker Dye as a Marker of Cellular Proliferation Indicator cells are incubated in the presence of a selected γc-cytokine or in the presence of a selected γc-cytokine and a selected custom derivative peptide. The cell population is then labeled in vitro using a cell-tracker dye, for example, CMFDA, C2925 from Invitrogen, and the decay of cellular green fluorescence at each cellular division is monitored using a flow-cytometer (for example, Beckton-Dickinson FACScalibur). Typically, in response to γc-cytokine stimulation 7~10 different peaks corresponding to the number of divisions that the cells have undergone will appear on the green fluorescence channel. Incubation of the cells with the selected γc-cytokine and antagonist custom derivative peptide reduces the number of peaks to only 1 to 3, depending on the degree of the inhibition.

Example 5—Inhibition of Intracellular Signaling by BNZ-γ and its Derivative Antagonists In addition to stimulating cellular proliferation, binding of the γc-cytokines to their receptors causes a diverse array of intracellular events. (Rochman et al. 2009 Nat. Rev. Immunol. 9:480-90, Pesu et al. 2005 Immunol. Rev. 203:127-142.) Immediately after the cytokine binds to its receptor, a tyrosine kinase called Jak3 (Janus-kinase 3) is recruited to the receptor at the plasma membrane. This kinase phosphorylates the tyrosine residues of multiple proteins including the γc-subunit, STAT5 (Signal Transducer and Activator of Transcription 5) and subunits of the PI3 (Phosphatidylinositol 3) kinase. Among these, the phosphorylation of STAT5 has been implicated in many studies as being linked to the proliferation of cells initiated by the γc-cytokine. (Reviewed in Hennighausen and Robinson, 2008 Genes Dev. 22:711-21.) In accordance with these published data, whether or not the BNZ-γ peptide inhibits the tyrosine phosphorylation of STAT5 molecule in PT-18β cells stimulated by IL-15 was examined (results shown in FIG. 3C).

PT-18β cells were stimulated by IL-15 in the presence or absence of BNZ-γ peptide. Cytoplasmic proteins were extracted from the cells according to a conventional method as described in Tagaya et al. 1996 EMBO J. 15:4928-39. The extracted cytoplasmic proteins were resolved using a standard SDS-PAGE (Sodium Dodecyl-Sulfate PolyAcrylamide Gel Electrophoresis) and the phorphorylation status was confirmed by an anti-phospho-STAT5 antibody (Cell Signaling Technology, Catalog #9354, Danvers Mass.) using immunoblotting (see FIG. 3C, top panel). To confirm that each lane represented a similar total protein load, the membrane was then stripped, and re-probed with an anti-STAT5 antibody (Cell Signaling Technology, Catalog #9358) (see FIG. 3C, bottom panel).

These results demonstrated that tyrosine phosphorylation of STAT5, a marker of signal transduction, was induced by IL-15 in PT-18β cells, and tyrosine phosphorylation of STAT5 was markedly reduced by the BNZ-γ peptide.

Example 6—Rational Design for BNZ-γ Derivative Antagonistic Peptides

Derivative peptides are prepared based from the core sequence D/E-F-L-E/Q/N-S/R-X-I/K-X-L/I-X-Q (SEQ ID NO: 2) (where X denotes any amino acid) by substituting the defined amino acids of the core sequence with amino acids having identical physico-chemical properties as designated in FIG. 2.

Alternatively, custom peptides or their derivative peptides can be prepared based on the sequence alignment of the D-helix regions of different γc-cytokine family members. For example, as shown in FIG. 5, one or more sequences conserved in γc-cytokine family (SEQ ID NO: 4-SEQ ID NO: 9) members can be combined to form a peptide such as SEQ ID NO: 3.

Example 7—Method of Identifying the Inhibitory Specificity of Antagonistic Custom Derivative Peptides The γc-cytokine inhibitory specificity of antagonistic custom derivative peptides is determined by assaying the ability of a custom derivative peptide to inhibit the proliferative response of a cytokine-responsive cell line to each of the 6 γc-cytokines. For example, a mouse cell line, CTLL-2, is used to determine if a candidate peptide inhibits the function of IL-2 and IL-15. PT-18(β) cells are used to determine if a candidate peptide inhibits the function of IL-4 and IL-9. PT-18 (7α) cells are used to determine if a candidate peptide inhibits the function of IL-7, and PT-18(21α) cells are used to determine if a candidate peptide inhibits the function of IL-21. PT-18(β) denotes a subclone of PT-18 cells that exogenously express human IL-2Rβ by gene transfection (See Tagaya et al. 1996), PT-18(7α) denotes a subclone that expresses human IL-7Rα by gene transfection and PT-18 (21Rα) cells express human IL-21Rα.

Another alternative is to use other cell lines that respond to an array of cytokines. An example of this cell line in a human NK cell line NK92 that is commercially available by ATCC (catalog # CRL-2407). This cell line is an IL-2 dependent cell line that responds to other cytokines including IL-9, IL-7, IL-15, IL-12, IL-18, IL-21 (Gong et al. 1994 Leukemia 8: 652-658, Kingemann et al., 1996, Biol Blood Marrow Transplant 2:68; 75, Hodge D L et al., 2002 J. Immunol. 168:9090-8)

Example 8—Preparation of γc-Antagonist Peptides

Custom derivative γc-antagonist peptides are synthesized chemically by manual and automated processes.

Manual synthesis: Classical liquid-phase synthesis is employed, which involves coupling the carboxyl group or C-terminus of one amino acid to the amino group or N-terminus of another. Alternatively, solid-phase peptide synthesis (SPPS) is utilized.

Automated synthesis: Many commercial companies provide automated peptide synthesis for a cost. These companies use various commercial peptide synthesizers, including synthesizers provided by Applied Biosystems (ABI). Custom derivative γc-antagonist peptides are synthesized by automated peptide synthesizers.

Example 9—Biological Production of Custom Derivative γc-Antagonist Peptides Using Recombinant Technology A custom derivative γc-antagonist peptides is synthesized biologically as a pro-peptide that consists of an appropriate tagging peptide, a signal peptide, or a peptide derived from a known human protein that enhances or stabilizes the structure of the BNZ-γ peptide or a peptide comprising the sequence of SEQ ID NO: 3 or a derivative thereof, and improves their biological activities. If desired, an appropriate enzyme-cleavage sequence proceeding to the N-terminus of the peptide shall be designed to remove the tag or any part of the peptide from the final protein.

A nucleotide sequence encoding the custom derivative peptide with a stop codon at the 3' end is inserted into a commercial vector with a tag portion derived from thioredoxin of E. coli and a special peptide sequence that is recognized and digested by an appropriate proteolytic enzyme (for example, enterokinase) intervening between the tag portion and the nucleotide sequence encoding the custom derivative peptide and stop codon. One example of a suitable vector is the pThioHis plasmid available from Invitrogen, CA. Other expression vectors may be used.

Example 10—Conjugation of Custom Peptides and Derivative to Carrier Proteins for Immunization Purposes and Generation of Antibody Against the Custom Peptides BNZ-γ and other custom derivative peptides, such as a peptide comprising the sequence of SEQ ID NO: 3 or a derivative thereof are used to immunize animals to obtain polyclonal and monoclonal antibodies. Peptides are conjugated to the N- or the C-terminus of appropriate carrier proteins (for example, bovine serum albumin, Keyhold Limpet Hemocyanin (KLH), etc.) by conventional methods using Glutaraldehyde or m-Maleimidobenzoyl-N-Hydroxysuccinimide Ester. The conjugated peptides in conjunction with an appropriate adjuvant are then used to immunize animals such as rabbits, rodents, or donkeys. The resultant antibodies are examined for specificity using conventional methods. If the resultant antibodies react with the immunogenic peptide, they are then tested for the ability to inhibit individual γc-cytokine activity according to the cellular proliferation assays described in Examples 1-3. Due to the composite nature of the derivative peptides it is possible to generate a single antibody that recognizes two different cytokines simultaneously, because of the composite nature of these peptides.

Example 11—Method for Large Scale Production of Custom Derivative γc-Antagonist Peptides Recombinant proteins are produced in large scale by the use of cell-free system as described elsewhere. (See Takai et al., 2010 Curr. Pharm. Biotechnol. 11(3):272-8.) Briefly, cDNAs encoding the γc-antagonist peptide and a tag are subcloned into an appropriate vector (See Takai et al., 2010 Curr. Pharm. Biotechnol. 11(3):272-8), which is subjected to in vitro transcription, followed immediately by an in vitro translation to produce the tagged peptide. The pro-polypeptide is then purified using an immobilized antibody recognizing the tagged epitope, treated by the proteolytic enzyme and the eluate (which mostly contains the custom derivative peptide of interest) is tested for purity using conventional 18% Tricine-SDS-PAGE (Invitrogen) and conventional comassie staining. Should the desired purity of the peptide not be met (>98%), the mixture is subjected to conventional HPLC (high-performance liquid chromatography) for further purification.

Example 12—Use of Custom Derivative γc-Antagonist Peptides to Block Cytokine Function in HAM/TSP HTLV-1—associated myelopathy (HAM)/tropical spastic paraparesis (TSP) is a chronic progressive myelopathy seen in some people infected with Human T-Lymphotropic Virus Type I (HTLV-I). Infiltration of lymphocytes in the spinal cord is associated with the immune response to HTLV-I and results in the release of certain cytokines. Some of these cytokines may also damage nerves.

Patients with HAM/TSP show an elevated state of the immune system that is similar to that observed in autoimmune diseases (Oh et al. 2008 Neurol Clin. 26:781-785). This elevated state is demonstrated by the ability of HAM/TSP patient's T-cells to undergo spontaneous proliferation in an ex vivo culture for about a week in the absence of exogenously added cytokines. The spontaneous proliferation of T-cells in HAM/TSP patients is attributed, at least partly, to autocrine/paracrine loops of IL-2, IL-9, and IL-15. It has been shown that adding blocking antibody against the IL-2 or IL-15 receptors can inhibit spontaneous T-cell proliferation in a HAM/TSP ex vivo culture system.

These observations, along with other data derived from ex vivo studies, have provided the rationale for taking two monoclonal antibodies (an anti-IL-2 receptor alpha or anti-Tac and an anti-IL-15 receptor beta chain) into the clinic for treatment of HAM/TSP (Azimi et al. 2001 Proc. Natl. Acad. Sci. 98:14559-64, Azimi et al., 1999 J. Immunol 163:4064-72).

Anti-cytokine receptor antagonists according to the embodiments described herein, would not only be valuable as a therapeutic immuno-modulatory agent for treatment of HAM/TSP, but modulation of immune response in HAM/TSP by anti-cytokine receptor antagonists according to the present embodiments acts proof-of-concept for the use of the anti-cytokine receptor antagonists according to the present embodiments in the treatment of other auto-immune diseases.

To demonstrate the efficacy of custom derivative γc-antagonist peptides according to the embodiments described herein, we tested the ability of BNZ-γ peptide to block immune response to HTLV-I in a spontaneous T-cell proliferation assay using a HAM/TSP ex vivo culture system. Proliferation assays were performed on HAM/TSP patient blood samples with and without the addition of BNZ-γ. These assays evaluated the ability of BNZ-γ to block the function of cytokines, such as IL-2 and IL-15, present in the ex vivo HAM/TSP patient blood culture and prevent spontaneous T-cell proliferation in these samples.

In an ex vivo spontaneous T-cell proliferation assay, PBMC from HAM/TSP patient was cultured at 1×10(6) cells per well of a 96 well plate in RPMI-10% FCS. Increasing concentrations of BNZ-γ peptide were added to each well. As a control, an irrelevant peptide was used in similar fashion. The cells were incubated in a 37° C. CO2 incubator for 3, 4, and 6 days. The amount of 1 uCi of $^3$H-thymidine was added to the cells. After an additional 6 hour incubation, cells were harvested their proliferation rate was measured. The data for a representative HAM/TSP patient is shown in FIG. 4A-FIG. 4D. As indicated in FIG. 4A-FIG. 4D, BNZ-γ peptide inhibits the spontaneous proliferation of T-cells in HAM/TSP culture at a concentration of about 1 ug/ml.

Other immunological markers were additionally measured in this assay. The percentage of the viral specific CD8 cells was measured during the ex vivo culture using viral protein tetramers. The population of CD4+CD25+ cells, a marker of T-cell activation, as well as Ki67 staining, a marker of T-cell proliferation, was monitored in a flow cytometry assay.

Other forms of the conjugated BNZ-γ peptide derivative or a custom peptide comprising the sequence of SEQ ID NO: 3, and a derivative thereof can be used in a similar future assay. They include albumin, BSA, PEG that can be conjugated to the peptide after chemical synthesis. Other biological forms of custom peptides such as the BNZ-γ peptide conjugate or a custom peptide comprising the sequence of SEQ ID NO: 3, and a derivative thereof may include regions of known protein entities (including but not limited to Fc region of human IgG) that are fused to the custom peptides.

Example 13—Method of Treating Adult T-Cell Leukemia (ATL) in a Human Patient by Administration of Custom Derivative γc-Antagonist Peptide A human patient suffering from Adult T-cell Leukemia is identified. An effective dose, as determined by the physician, of custom derivative γc-antagonist peptide, for example, BNZ-γ, a custom peptide comprising the sequence of SEQ ID NO: 3, or a derivative thereof is administered to the patient for a period of time determined by the physician. Treatment is determined to be effective if patient enters remission.

Example 14—Method of Treating HAM/TSP in a Human Patient by Administration of Custom Derivative γc-Antagonist Peptide A human patient suffering from HAM/TSP is identified. An effective dose, as determined by the physician, of custom derivative γc-antagonist peptide, for example, BNZ-γ, a custom peptide comprising the sequence of SEQ ID NO: 3, or a derivative thereof is administered to the patient for a period of time determined by the physician. Treatment is determined to be effective if patient's symptoms improve or if the progression of the disease has been stopped or slowed down.

Example 15—Use of Custom Derivative γc-Antagonist Peptides to Block Cytokine Function A human patient suffering who is in need of reducing the function of at least IL-15 and IL-21 is identified. An effective dose, as determined by the physician, of custom derivative γc-antagonist peptide, for example, a composite peptide comprising the sequence of SEQ ID NO: 3 or a derivative thereof is administered to the patient for a period of time determined by the physician. Treatment is determined to be effective if patient's symptoms improve or if the progression of the disease has been stopped or slowed down.

Example 16—Method of Treating Celiac Disease in a Human Patient by Administration of Custom Derivative γc-Antagonist Peptide A human patient suffering from Celiac disease is identified. An effective dose, as determined by the physician, of custom derivative γc-antagonist peptide, for example, a composite peptide comprising the sequence of SEQ ID NO: 3 or a derivative thereof is administered to the patient for a period of time determined by the physician. Treatment is determined to be effective if patient's symptoms improve or if the progression of the disease has been stopped or slowed down.

REFERENCES

Antony, P. A., Paulos, C. M., Ahmadzadeh, M., Akpinarli, A., Palmer, D. C., Sato, N., Kaiser A., Heinrichs, C. S., Klebanoff, C. A., Tagaya, Y., and Restifo, N P., Interleukin-2-dependent mechanisms of tolerance and immunity in vivo. 2006 J. Immunol. 176:5255-66.

Azimi, N., Nagai, M., Jacobson, S., Waldmann, T. A., IL-15 plays a major role in the persistence of Tax-specific CD8 cells in HAM/TSP patients. 2001 Proc. Natl. Acad. Sci. 98:14559-64.

Azimi, N., Mariner J., Jacobson S., Waldmann T. A., How does interleukin 15 contribute to the pathogenesis of HTLV type-1 associated myelopathy/tropical spastic paraparesis? 2000 AIDS Res. Hum. Retroviruses 16:1717-22.

Azimi, N., Jacobson, S., Leist, T., Waldmann, T. A., Involvement of IL-15 in the pathogenesis of human T lymphotropic virus type-I-associated myelopathy/tropical spastic paraparesis: implications for therapy with a monoclonal antibody directed to the IL-2/15R beta receptor. 1999 J. Immunol. 163:4064-72.

Azimi, N., Brown, K., Bamford, R. N., Tagaya, Y., Siebenlist, U., Waldmann, T. A., Human T cell lymphotropic virus type I Tax protein trans-activates interleukin 15 gene transcription through an N F-kappaB site. 1998 Proc. Natl. Acad. Sci. USA 95:2452-7.

Bazan, J. F., Hematopoietic receptors and helical cytokines. 1990 Immunol. Today 11:350-354.

Bettini, M., and Vignali, D. A., Regulatory T cells and inhibitory cytokines in autoimmunity. 2009 Curr. Opin. Immunol. 21:612-8.

Bodd, M., Raki, M., Tollefsen, S., Fallang, L. E., Bergseng, E., Lundin, K. E., Sollid, L. M., HLA-DQ2-restricted gluten-reactive T cells produce IL-21 but not IL-17 or IL-22. 2010 Mucosal Immunol. 3:594-601.

De Rezende, L. C., Silva I. V., Rangel, L. B., Guimaraes, M. C., Regulatory T cells as a target for cancer therapy. 2010 Arch. Immunol. Ther. Exp. 58:179-90.

Dubois, S., Mariner, J., Waldmann, T. A., Tagaya, Y., IL-15Ralpha recycles and presents IL-15 In trans to neighboring cells. 2002 Immunity 17:537-47.

Dodge D L. Et al., IL-2 and IL-12 alter N K cell responsiveness to IFN-gamma-inducible protein 10 by down-regulating CXCR3 expression. J. Immun. 168:6090-8.

Fehniger, T. A., Suzuki, K., Ponnappan, A., VanDeusen, J. B., Cooper, M. A., *Florea*, S. M., Freud, A. G., Robinson, M. L., Durbin, J., Caligiuri, M. A., Fatal leukemia in interleukin 15 transgenic mice follows early expansions in natural killer and memory phenotype CD8+ T cells. 2001 J. Exp. Med. 193:219-31.

Fisher, A. G., Burdet, C., LeMeur, M., Haasner, D., Gerber, P., Cerediq, R., Lymphoproliferative disorders in an IL-7 transgenic mouse line. 1993 Leukemia 2:S66-68.

Gong J H, et al. Characterization of a human cell line (INK-92) with phenotypical and functional characteristics of activated natural killer cells. Leukemia 8: 652-658, 1994.

Hennighausen, L., Robinson, G. W., Interpretation of cytokine signaling through the transcription factors STAT5A and STAT5B. 2008 Genes Dev. 22:711-21.

Kiingemann H G, et al. A cytotoxic N K-cell line (NK-92) for ex vivo purging of leukemia from blood. Biol. Blood Marrow Transplant. 2: 68-75, 1996.

Krause, C. D. and Pestka, S., Evolution of the Class 2 cytokines and receptors, and discovery of new friends and relatives. 2005 Pharmacol. and Therapeutics 106:299-346.

Kundig, T. M., Schorle, H., Bachmann, M. F., Hengartener, H., Zinkernagel, R. M., Horak, I., Immune Responses of the interleukin-2-deficient mice. 1993 Science 262:1059-61.

Le Buanec, H., Paturance, S., Couillin, I., Schnyder-Candrian, S., Larcier, P., Ryffel, B., Bizzini, B., Bensussan, A., Burny, A., Gallo, R., Zagury, D., Peltre, G., Control of allergic reactions in mice by an active anti-murine IL-4 immunization. 2007 Vaccine 25:7206-16.

Littman, D. R., Rudensky, A Y., Th17 and regulatory T cells in mediating and restraining inflammation. 2010 Cell 140(6):845-58.

Miyagawa, F., Tagaya, Y., Kim, B. S., Patel, H. J., Ishida, K., Ohteki, T., Waldmann, T. A., Katz, S. I., IL-15 serves as a costimulator in determining the activity of autoreactive CD8 T cells in an experimental mouse model of graft-versus-host-like disease. 2008 J. Immunol. 181:1109-19.

Noguchi, M., Yi, H., Rosenblatt, H. M., Filipovich, A. H., Adelstein, S., Modi, W. S., McBride, O. W., Leonard, W. J., Interleukin 2 receptor gamma chain mutation results in X-linked severe combined immunodeficiency in humans. 1993 Cell 73:147-157.

O H, U., Jacobson S., Treatment of HTLV-I-Associated Myelopathy/Tropical Spastic Paraparesis: Towards Rational Targeted Therapy 2008 Neurol Clin. 2008 26: 781-785.

Orzaez, M., Gortat, A., Mondragon, L., Perez-Paya, E., Peptides and Peptide Mimics as Modulators of Apototic Pathways. 2009 Chem. Med. Chem. 4:146-160.

O'Shea, J. J., Targeting the Jak/STAT pathway for immunosuppression. 2004 Ann. Rheum. Dis. 63: (suppl II): ii67-71.

Paul, W. E., Pleiotropy and redundancy: T cell-derived lymphokines in the immune response. 1989 Cell 57:521-4.

Pesu M, Candotti F, Husa M, Hofmann S R, Notarangelo L D, and O'Shea J J. Jak3, severe combined immunodeficiency, and a new class of immunosuppressive drugs. 2005 Immunol. Rev. 203:127-142.

Pesu, M., Laurence, A., Kishore, N., Zwillich, S., Chan, G., O'Shea, J. J., Therapeutic targeting of Janus kinases. Immunol. 2008 Rev. 223:132-142.

Rochman, Y., Spolski, R., Leonard, W. J., New Insights into the regulation of T cells by gamma c family cytokines. 2009 Nat. Rev. Immunol. 9:480-90.

Sakaguchi, S., Yamaguchi, T., Nomura, T., Ono, M., Regulatory T cells and immune tolerance. 2008 Cell 133: 775-87.

Sato, N., Sabzevari, H., Fu, S., Ju, W., Bamford, R. N., Waldmann, T. A., and Tagaya, Y., Development of an IL-15-Autocrine CD8 T-cell Leukemia in IL-15 Transgenic mice requires the cis-expression of IL-15R apha. Blood 2011 in press.

Sugamura, K., Asao, H., Kondo, M., Tanaka, N., Ishii, N., Nakamura, M., Takeshita, T., The common gamma-chain for multiple cytokine receptors. 1995 Adv. Immunol. 59: 225-277.

Sugamura, K., Asao, H., Kondo, M., Tanaka, N., Ishii, N., Ohbo, K., Nakamura, M., Takeshita, T., The interleukin-2 receptor gamma chain: its role in the multiple cytokine receptor complexes and T cell development in XSCID. 1996 Annu. Rev. Immunol. 14:179-205.

Tagaya, Y., Burton, J. D., Miyamoto, Y., Waldmann, T A., Identification of a novel receptor/signal transduction pathway for IL-15/T in mast cells. 1996 EMBO J. 15:4928-39.

Tagaya, Y., Memory CD8 T cells now join "Club 21". 2010 J. Leuk. Biol. 87:13-15.

Takai, K., Sawasaki, T., and Endo. Y. The Wheat-Germ Cell-Free Expression System, 2010 Curr. Pharm. Biotechnol. 11:272-8.

Tanaka, T., et al., A novel monoclonal antibody against murine IL-2 receptor beta-chain. Characterization of receptor expression in normal lymphoid cells and EL-4 cells. 1991 J. Immunol. 147:2222-28.

Takeshita, T., Asao, H., Ohtani, K., Ishii, N., Kumaki, S., Tanaka, N., Manukata, H., Nakamura, M., Sugamura, K., Cloning of the Gamma chain of the Human IL2 receptor. 1992 Science 257:379-382.

Waldmann, T. A., Anti-Tac (daclizumab, Zenapax) in the treatment of leukemia, autoimmune diseases, and in the prevention of allograft rejection: a 25-year personal odyssey. 2007 J. Clin. Immunol. 27: 1-18.

---

What is claimed is:

1. A kit for treating a condition in a patient, wherein the condition is a γc cytokine-mediated disease, an human T-lymphotropic virus (HTLV)-1-associated myelopathy (HAM)/tropical spastic paraparesis (TSP) associated disease, an inflammatory respiratory disease, a cosmetic condition, or a combination thereof, the kit comprising a pharmaceutical composition, wherein the pharmaceutical composition comprises:

a therapeutically effective amount of a peptide conjugate, or a derivative thereof; and a pharmaceutically acceptable carrier, diluent, excipient or combination thereof;

wherein the peptide conjugate or the derivative thereof modulates the activity of two or more γc-cytokines selected from the group consisting of interleukin (IL)-15 and IL-21;

wherein the peptide conjugate comprises the amino acid sequence P-K-E-F-L-E-R-F-V-H-L-V-Q-M-F-I-H-Q-S-L-S(SEQ ID NO: 3); and wherein the derivative thereof comprises a peptide sequence sharing at least 90% identity with the amino acid sequence of SEQ ID NO: 3.

2. The kit of claim 1, wherein the condition is one or more of CD4 leukemia, CD8 leukemia, LGL leukemia, systemic lupus erythematosus, Sjögren's syndrome, Wegener's granulomatosis, Celiac disease, Hashimoto's thyroiditis, rheumatoid arthritis, inflammatory bowel disease, diabetes mellitus, psoriasis, multiple sclerosis, uveitis, inflammation of the eye, graft-versus-host disease (GvHD), Adult T-cell Leukemia (ATL), HTLV-associated Myelopathy/Tropical Spastic Paraparesis (HAM/TSP), and other non-neoplastic inflammatory diseases associated with HTLV, including uveitis (HU), arthropathy, pneumopathy, dermatitis, exocrinopathy, myositis, asthma, sinusitis, hay fever, bronchitis, chronic obstructive pulmonary disease (COPD), allergic rhinitis, acute and chronic otitis, and lung fibrosis, acne, hair loss, sunburn, nail maintenance, or appearance of aging.

3. A method for blocking signaling by two or more γc-cytokine family members, comprising contacting a cell with the pharmaceutical composition of the kit of claim 1.

4. A method of inhibiting γc-cytokine binding to a γc-subunit, comprising contacting a γc-subunit of a cell with the pharmaceutical composition of the kit of claim 1.

5. A method of treating a γc-cytokine-mediated disease, the method comprising administering the pharmaceutical composition of the kit of claim 1 to a subject in need thereof, wherein the γc-cytokine-mediated disease is selected from the group consisting of CD4-leukemia, CD8-leukemia, LGL-leukemia, systemic lupus erythematosus, Sjögren's syndrome, Wegener's granulomatosis, Celiac disease, Hashimoto's thyroiditis, rheumatoid arthritis, diabetes mellitus, psoriasis, multiple sclerosis, uveitis, inflammation of the eye, and graft-versus-host disease (GvHD).

6. A method of treating an HTLV-1 associated myelopathy (HAM)/tropical spastic paraparesis (TSP) associated disease, the method comprising administering the pharmaceutical composition of the kit of claim 1 to a subject in need thereof, wherein the HAM/TSP associated disease is selected from the group consisting of Adult T-cell Leukemia (ATL), HTLV-associated Myelopathy/Tropical Spastic Paraparesis (HAM/TSP), and other non-neoplastic inflammatory diseases associated with HTLV, including uveitis (HU), arthropathy, pneumopathy, dermatitis, exocrinopathy, and myositis.

7. A method of treating an inflammatory respiratory disease, the method comprising administering the pharmaceutical composition of the kit of claim 1 to a subject in need thereof, wherein the inflammatory respiratory disease is selected from the group consisting of asthma, sinusitis, hay fever, bronchitis, chronic obstructive pulmonary disease (COPD), allergic rhinitis, acute and chronic otitis, and lung fibrosis.

8. A method of treating a cosmetic condition, the method comprising administering the pharmaceutical composition of the kit of claim 1 to a subject in need thereof, wherein the cosmetic disease is selected from the group consisting of acne, hair loss, sunburn, nail maintenance, and appearance of aging.

* * * * *

SEQUENCE LISTING

```
<160> NUMBER OF SEQ ID NOS: 11

<210> SEQ ID NO 1
<211> LENGTH: 19
<212> TYPE: PRT
<213> ORGANISM: Artificial
<220> FEATURE:
<223> OTHER INFORMATION: Synthetic

<400> SEQUENCE: 1

Ile Lys Glu Phe Leu Gln Arg Phe Ile His Ile Val Gln Ser Ile Ile
1               5                   10                  15

Asn Thr Ser

<210> SEQ ID NO 2
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = D or E
<220> FEATURE:
<221> NAME/KEY: MISC_FEATURE
<222> LOCATION: (4)..(4)
<223> OTHER INFORMATION: X = E or Q or N
```

```
<220> FEATURE:
<221> NAME/KEY: MISC_FEATURE
<222> LOCATION: (5)..(5)
<223> OTHER INFORMATION: X = S or R
<220> FEATURE:
<221> NAME/KEY: MISC_FEATURE
<222> LOCATION: (6)..(6)
<223> OTHER INFORMATION: X = Any amino acid
<220> FEATURE:
<221> NAME/KEY: MISC_FEATURE
<222> LOCATION: (7)..(7)
<223> OTHER INFORMATION: X = I or K
<220> FEATURE:
<221> NAME/KEY: MISC_FEATURE
<222> LOCATION: (8)..(8)
<223> OTHER INFORMATION: X = Any amino acid
<220> FEATURE:
<221> NAME/KEY: MISC_FEATURE
<222> LOCATION: (9)..(9)
<223> OTHER INFORMATION: X = L or I
<220> FEATURE:
<221> NAME/KEY: MISC_FEATURE
<222> LOCATION: (10)..(10)
<223> OTHER INFORMATION: X = Any amino acid

<400> SEQUENCE: 2

Xaa Phe Leu Xaa Xaa Xaa Xaa Xaa Xaa Gln
1               5                   10

<210> SEQ ID NO 3
<211> LENGTH: 21
<212> TYPE: PRT
<213> ORGANISM: Artificial
<220> FEATURE:
<223> OTHER INFORMATION: Synthetic

<400> SEQUENCE: 3

Pro Lys Glu Phe Leu Glu Arg Phe Val His Leu Val Gln Met Phe Ile
1               5                   10                  15

His Gln Ser Leu Ser
            20

<210> SEQ ID NO 4
<211> LENGTH: 19
<212> TYPE: PRT
<213> ORGANISM: Artificial
<220> FEATURE:
<223> OTHER INFORMATION: Synthetic

<400> SEQUENCE: 4

Ile Lys Glu Phe Leu Gln Ser Phe Val His Ile Val Gln Met Phe Ile
1               5                   10                  15

Asn Thr Ser

<210> SEQ ID NO 5
<211> LENGTH: 20
<212> TYPE: PRT
<213> ORGANISM: Artificial
<220> FEATURE:
<223> OTHER INFORMATION: Synthetic

<400> SEQUENCE: 5

Ile Val Glu Phe Leu Asn Arg Trp Ile Thr Phe Cys Gln Ser Ile Ile
1               5                   10                  15

Ser Thr Leu Thr
            20

<210> SEQ ID NO 6
```

```
<211> LENGTH: 21
<212> TYPE: PRT
<213> ORGANISM: Artificial
<220> FEATURE:
<223> OTHER INFORMATION: Synthetic

<400> SEQUENCE: 6

Pro Lys Glu Phe Leu Glu Arg Phe Lys Ser Leu Leu Gln Lys Met Ile
1               5                   10                  15

His Gln His Leu Ser
            20

<210> SEQ ID NO 7
<211> LENGTH: 21
<212> TYPE: PRT
<213> ORGANISM: Artificial
<220> FEATURE:
<223> OTHER INFORMATION: Synthetic

<400> SEQUENCE: 7

Leu Glu Asn Phe Leu Glu Arg Leu Lys Thr Ile Met Arg Glu Lys Tyr
1               5                   10                  15

Ser Lys Cys Ser Ser
            20

<210> SEQ ID NO 8
<211> LENGTH: 21
<212> TYPE: PRT
<213> ORGANISM: Artificial
<220> FEATURE:
<223> OTHER INFORMATION: Synthetic

<400> SEQUENCE: 8

Ala Leu Thr Phe Leu Glu Ser Leu Leu Glu Leu Phe Gln Lys Glu Lys
1               5                   10                  15

Met Arg Gly Met Arg
            20

<210> SEQ ID NO 9
<211> LENGTH: 20
<212> TYPE: PRT
<213> ORGANISM: Artificial
<220> FEATURE:
<223> OTHER INFORMATION: Synthetic

<400> SEQUENCE: 9

Asp Leu Cys Phe Leu Lys Arg Leu Leu Gln Glu Ile Lys Thr Cys Trp
1               5                   10                  15

Asn Lys Ile Leu
            20

<210> SEQ ID NO 10
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = Any amino acid
<220> FEATURE:
<221> NAME/KEY: MISC_FEATURE
<222> LOCATION: (2)..(2)
<223> OTHER INFORMATION: X = Any amino acid
<220> FEATURE:
<221> NAME/KEY: MISC_FEATURE
```

```
<222> LOCATION: (3)..(3)
<223> OTHER INFORMATION: X = D or E
<220> FEATURE:
<221> NAME/KEY: MISC_FEATURE
<222> LOCATION: (6)..(6)
<223> OTHER INFORMATION: X = E or Q or N or polar amino acid
<220> FEATURE:
<221> NAME/KEY: MISC_FEATURE
<222> LOCATION: (7)..(7)
<223> OTHER INFORMATION: X = S or R or polar amino acid
<220> FEATURE:
<221> NAME/KEY: MISC_FEATURE
<222> LOCATION: (8)..(8)
<223> OTHER INFORMATION: X = Non-polar amino acid
<220> FEATURE:
<221> NAME/KEY: MISC_FEATURE
<222> LOCATION: (9)..(9)
<223> OTHER INFORMATION: X = I or K or non-polar amino acid
<220> FEATURE:
<221> NAME/KEY: MISC_FEATURE
<222> LOCATION: (10)..(10)
<223> OTHER INFORMATION: X = Any amino acid
<220> FEATURE:
<221> NAME/KEY: MISC_FEATURE
<222> LOCATION: (11)..(11)
<223> OTHER INFORMATION: X = L or I or aliphatic amino acid
<220> FEATURE:
<221> NAME/KEY: MISC_FEATURE
<222> LOCATION: (12)..(12)
<223> OTHER INFORMATION: X = Non-polar amino acid
<220> FEATURE:
<221> NAME/KEY: MISC_FEATURE
<222> LOCATION: (14)..(14)
<223> OTHER INFORMATION: X = Charged amino acid
<220> FEATURE:
<221> NAME/KEY: MISC_FEATURE
<222> LOCATION: (15)..(15)
<223> OTHER INFORMATION: X = Any amino acid
<220> FEATURE:
<221> NAME/KEY: MISC_FEATURE
<222> LOCATION: (16)..(16)
<223> OTHER INFORMATION: X = I or K
<220> FEATURE:
<221> NAME/KEY: MISC_FEATURE
<222> LOCATION: (17)..(17)
<223> OTHER INFORMATION: X = Any amino acid
<220> FEATURE:
<221> NAME/KEY: MISC_FEATURE
<222> LOCATION: (18)..(18)
<223> OTHER INFORMATION: X = Any amino acid
<220> FEATURE:
<221> NAME/KEY: MISC_FEATURE
<222> LOCATION: (19)..(19)
<223> OTHER INFORMATION: X = Any amino acid

<400> SEQUENCE: 10

Xaa Xaa Xaa Phe Leu Xaa Xaa Xaa Xaa Xaa Xaa Xaa Gln Xaa Xaa Xaa
1               5                   10                  15

Xaa Xaa Xaa

<210> SEQ ID NO 11
<211> LENGTH: 19
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X = Any amino acid
```

```
<220> FEATURE:
<221> NAME/KEY: MISC_FEATURE
<222> LOCATION: (2)..(2)
<223> OTHER INFORMATION: X = Any amino acid
<220> FEATURE:
<221> NAME/KEY: MISC_FEATURE
<222> LOCATION: (3)..(3)
<223> OTHER INFORMATION: X = D or E
<220> FEATURE:
<221> NAME/KEY: MISC_FEATURE
<222> LOCATION: (6)..(6)
<223> OTHER INFORMATION: X = E or Q or N or polar amino acid
<220> FEATURE:
<221> NAME/KEY: MISC_FEATURE
<222> LOCATION: (7)..(7)
<223> OTHER INFORMATION: X = S or R or polar amino acid
<220> FEATURE:
<221> NAME/KEY: MISC_FEATURE
<222> LOCATION: (8)..(8)
<223> OTHER INFORMATION: X = Non-polar amino acid
<220> FEATURE:
<221> NAME/KEY: MISC_FEATURE
<222> LOCATION: (9)..(9)
<223> OTHER INFORMATION: X = I or K or non-polar amino acid
<220> FEATURE:
<221> NAME/KEY: MISC_FEATURE
<222> LOCATION: (10)..(10)
<223> OTHER INFORMATION: X = Any amino acid
<220> FEATURE:
<221> NAME/KEY: MISC_FEATURE
<222> LOCATION: (11)..(11)
<223> OTHER INFORMATION: X = L or I or aliphatic amino acid
<220> FEATURE:
<221> NAME/KEY: MISC_FEATURE
<222> LOCATION: (12)..(12)
<223> OTHER INFORMATION: X = Non-polar amino acid
<220> FEATURE:
<221> NAME/KEY: MISC_FEATURE
<222> LOCATION: (14)..(14)
<223> OTHER INFORMATION: X = Charged amino acid
<220> FEATURE:
<221> NAME/KEY: MISC_FEATURE
<222> LOCATION: (15)..(15)
<223> OTHER INFORMATION: X = Any amino acid
<220> FEATURE:
<221> NAME/KEY: MISC_FEATURE
<222> LOCATION: (17)..(17)
<223> OTHER INFORMATION: X = Any amino acid

<400> SEQUENCE: 11

Xaa Xaa Xaa Phe Leu Xaa Xaa Xaa Xaa Xaa Xaa Xaa Gln Xaa Xaa Ile
1               5                   10                  15

Xaa Thr Ser
```